(12) United States Patent
Matsumura et al.

(10) Patent No.: US 7,398,121 B2
(45) Date of Patent: Jul. 8, 2008

(54) IONTOPHORESIS DEVICE

(75) Inventors: Akihiko Matsumura, Minato-ku (JP); Sakae Torisawa, Urayasu (JP); Kiyoshi Kanamura, Hachioji (JP); Yoshihiro Ito, Kyoto (JP); Yoriko Kobayashi, Otsu (JP)

(73) Assignee: TTI ellebeau, Inc., Tokyo (JP)

( * ) Notice: Subject to any disclaimer, the term of this patent is extended or adjusted under 35 U.S.C. 154(b) by 213 days.

(21) Appl. No.: 10/488,970

(22) PCT Filed: May 15, 2002

(86) PCT No.: PCT/JP02/04696
§ 371 (c)(1),
(2), (4) Date: Aug. 24, 2004

(87) PCT Pub. No.: WO03/037425
PCT Pub. Date: May 8, 2003

(65) Prior Publication Data
US 2005/0070840 A1    Mar. 31, 2005

(30) Foreign Application Priority Data
Oct. 31, 2001   (JP)   ............................. 2001-335293

(51) Int. Cl.
*A61N 1/30*     (2006.01)
(52) U.S. Cl. ...................... 604/20; 604/890.1
(58) Field of Classification Search ............... 604/20, 604/890.1; 424/449
See application file for complete search history.

(56) References Cited

U.S. PATENT DOCUMENTS

| | | | |
|---|---|---|---|
| 4,722,726 A | 2/1988 | Sanderson et al. | |
| 4,731,049 A | 3/1988 | Parsi | |
| 4,744,787 A | 5/1988 | Phipps et al. | |
| 4,747,819 A | 5/1988 | Phipps et al. | |
| 4,927,408 A * | 5/1990 | Haak et al. | ............. 604/20 |
| 5,084,006 A | 1/1992 | Lew et al. | |
| 5,084,008 A | 1/1992 | Phipps | |

(Continued)

FOREIGN PATENT DOCUMENTS

EP    1 043 043 A1    12/1998

(Continued)

*Primary Examiner*—Nicholas D. Lucchesi
*Assistant Examiner*—Laura A Bouchelle
(74) *Attorney, Agent, or Firm*—Reed Smith LLP; Stanley P. Fisher, Esq.; Juan Carlos A. Marquez, Esq.

(57) ABSTRACT

An iontophoresis device useful for administering an ionic drug by iontophoresis has an iontophoresis electrode section (active electrode section) and a ground electrode section (inactive electrode section) both of which are to be connected to a power source. The iontophoresis device includes elements (members) of both of the electrode sections are all formed of membrane bodies, and includes ion exchange membranes different in ion selectivity, one being selective to ions of the same species as charged ions of the ionic drug and the other to ions different in species from the charged ions of the ionic drug that are arranged in the iontophoresis electrode section, and at least an ion exchange membrane selective to ions opposite to the charged ions of the ionic drug is arranged in the ground electrode section. The iontophoresis device can administer the ionic drug stably over a long period of time at high transport efficiency.

20 Claims, 6 Drawing Sheets

U.S. PATENT DOCUMENTS

| | | |
|---|---|---|
| 5,135,477 A | 8/1992 | Unterecker et al. |
| 5,162,043 A | 11/1992 | Lew et al. |
| 5,326,341 A | 7/1994 | Lew et al. |
| 5,395,310 A | 3/1995 | Untereker et al. |
| 5,405,317 A | 4/1995 | Myers et al. |
| 5,496,266 A | 3/1996 | Haak et al. |
| 5,503,682 A | 4/1996 | Mueller-Kirschbaum et al. |
| 5,543,098 A | 8/1996 | Myers et al. |
| 5,628,729 A | 5/1997 | Okabe |
| 5,647,844 A * | 7/1997 | Haak et al. .................. 604/20 |
| 5,668,170 A | 9/1997 | Gyory |
| 5,711,761 A | 1/1998 | Untereker et al. |
| 5,788,666 A | 8/1998 | Atanasoska |
| 5,817,044 A | 10/1998 | Evers et al. |
| 5,840,056 A | 11/1998 | Atanasoska |
| 5,871,460 A | 2/1999 | Phipps et al. |
| 5,908,400 A | 6/1999 | Higo et al. |
| 5,941,843 A | 8/1999 | Atanasoska et al. |
| 5,993,435 A | 11/1999 | Haak et al. |
| 6,064,908 A | 5/2000 | Muller et al. |
| 6,169,920 B1 | 1/2001 | Haak et al. |
| 6,377,847 B1 | 4/2002 | Keusch et al. |
| 6,553,255 B1 | 4/2003 | Miller et al. |
| 6,862,473 B2 | 3/2005 | Keusch et al. |
| 2002/0099320 A1 | 7/2002 | Beck |
| 2003/0065305 A1 | 4/2003 | Higuchi et al. |
| 2004/0167459 A1 | 8/2004 | Higuchi et al. |

FOREIGN PATENT DOCUMENTS

| | | |
|---|---|---|
| EP | 1 059 097 A1 | 2/1999 |
| EP | 1 177 814 A1 | 5/2000 |
| HU | 195922 A | 11/1987 |
| JP | 8-238325 | 6/1988 |
| JP | 3-94771 | 9/1989 |
| JP | 3-504343 | 10/1989 |
| JP | 4-297277 | 3/1991 |
| JP | 11-273452 | 3/1998 |
| JP | 11-128369 | 8/1998 |
| JP | 2000-229128 | 2/1999 |
| JP | 2000-229129 | 2/1999 |
| JP | 2000-237326 | 2/1999 |
| JP | 2000-237327 | 2/1999 |
| JP | 2000-237328 | 2/1999 |
| JP | 2000-237329 | 2/1999 |
| JP | 2000-288097 | 4/1999 |
| JP | 2000-288098 | 4/1999 |
| WO | WO 90/04433 | 10/1989 |
| WO | WO 99/33518 | 12/1998 |
| WO | WO 00/61218 | 4/2000 |
| WO | WO 00/69514 | 5/2000 |
| WO | WO 00/74772 | 6/2000 |
| WO | WO 03/037425 A1 | 5/2002 |

* cited by examiner

IONTOPHORESIS DEVICE

TECHNICAL FIELD

This invention relates to a device useful for transdermal administration (transdermal drug delivery) of various ionic drugs (ionic substances having desired medicinal efficacy) by iontophoresis (hereinafter called iontophoresis device).

More specifically, this invention relates to an iontophoresis device of high added value, which is constructed in such ways that an iontophoresis electrode section (active electrode section) and a ground electrode section (inactive electrode section) are constructed to assure a stably energized state (constant current and/or constant voltage) over a long period of time, and that a drug (active) ingredient of an ionic drug charged positive (+) or negative (−) at the iontophoresis electrode section is efficiently carried (driven) toward the skin (or the mucosa). In other words, a high transference number (transference percentage) is assured, and that the iontophoresis electrode section (active electrode section) and ground electrode section (inactive electrode section) contribute to the maintenance of the above-described stably energized state and prevent adverse effects to the skin, such as skin inflammation caused by electrode reaction.

BACKGROUND ART

A method of introducing (delivering) ionic drug (ionic chemical substance) placed at a desired part of the skin or mucosa (hereinafter simply called the skin) into the body through the skin by giving the skin an electromotive force sufficient to drive such ionic drug is called iontophoresis (ion introduction method or ion delivery treatment) (See, for example, JP-A-63035266 for the above-mentioned definition of iontophoresis).

As described above, iontophoresis performs desired medical treatment by driving (carrying) an ionizable or ionic drug, which has been applied on the skin, under predetermined electromotive force to deliver the same into the skin.

For example, positively charged ions are driven (carried) into the skin on the side of an anode in an electric system of an iontophoresis device.

Negatively charged ions, on the other hand, are driven (carried) into the skin on the side of a cathode in the electric system of the iontophoresis device.

The following are examples of ionic drugs to which the above-described iontophoresis is applicable.

(1) Positively Chargeable Ionic Drugs:

Local anesthetic drugs (procaine hydrochloride, lidocaine hydrochloride, etc.), gastrointestinal drugs (calnitine chloride, etc.), skeletal muscle relaxants (pancuronium bromide, etc.), and antibiotics (tetracycline derivatives, kanamycin derivatives, gentamicin derivatives).

(2) Negatively Chargeable Ionic Drugs:

Vitamins (hereinafter abbreviated as V) ($VB_2$, $VB_{12}$, VC, VE, folic acid, etc.), adrenocorticosteroids (hydrocortisone water soluble drugs, dexamethazone water soluble drugs, prednisolone water soluble drugs, etc.), and antibiotics (penicillins water soluble drugs, chloramphenicol water soluble drugs).

Concerning methods for administering ionic drugs by iontophoresis and devices to be used in the practice of such methods, research and development have been made for many years, and a variety of methods and devices have been proposed.

Conventional art on this type of iontophoresis includes those using ion exchange membranes. The present invention also belongs to the category of technology using ion exchange membranes as will be described in detail below.

To facilitate understanding of the present invention that makes use of ion exchange membranes, a detailed description of typical examples of the prior art using ion exchange membranes will be given below.

1. Japanese Language Laid-open Publication (PCT) No. HEI 3-504343 (International Publication No. WO90/04433), International Publication Date: May 3, 1990 (Hereinafter Called the Prior Art 1):

(1) The prior art 1 discloses an iontophoresis electrode, comprising (i) an electrode plate, (ii) a reservoir for storing an ionic (or ionizable) drug to be delivered, and (iii) an ion exchange membrane disposed on an outer side (skin-contacting side) of the reservoir and selective to ions charged in the same polarity as the ionic drug.

(2) In the prior art 1, the function of the ion exchange membrane is described that, in the process of carrying (driving) the ionic drug toward the skin, the ion exchange membrane restricts movement of ions which are charged electrically opposite to the ionic drug and move from the skin toward the electrode plate. For example, it inhibits movement of ion species existing on the skin such as sodium ions, chlorine ions and other ions which may form an ionic current path different from the current path formed by the ionic drug.

(3) The prior art 1 also describes that the efficiency of administration of the ionic drug is increased because the ion exchange membrane reduces migration of other mobile charge carriers into the reservoir containing the ionic drug.

2. U.S. Pat. No. 4,722,726 (Hereinafter Called the Prior Art 2):

(1) The prior art 2 is referred to as a related art in the patent specification of the prior art 1, and discloses an electrode of the following construction:

(i) the electrode is divided into a first chamber containing an electrolyte and a second chamber containing an ionized ingredient, and (ii) the first chamber and the second chamber are isolated from each other by an ion exchange membrane.

(2) The prior art 2 describes that the first chamber containing the electrolyte can lessen the deleterious effects of hydrolysis of water and that the ion exchange membrane can isolate the ionic drug from the electrolyte in the first chamber.

However, the technology disclosed in the prior art 2, which uses electrolyte, also has an undesirable facet that the efficiency of transport (transference number) of charged ions of the active ingredient in the ionic drug is apparently lowered, because it increases the concentration of other additional ion species in the system.

Therefore, care should be taken in adopting a technology which uses electrolyte in this way.

3. JP-A-03094771 (Hereinafter Called the Prior Art 3):

(1) The prior art 3 discloses an electrode for iontophoresis comprising (i) a water retaining portion surrounded by a flexible supporting member and having an electrode plate inside, (ii) an ion exchange membrane disposed on a front side (skin side) of the water-retaining portion, and (iii) a drug layer (ionic drug layer) disposed on a front side (skin side) of the ion exchange membrane.

(2) The prior art 3 is intended to administer an ionic drug of a high concentration while preventing dilution of the drug with water in the course of administration of the drug.

(3) For this purpose, the prior art 3 discloses an iontophoresis electrode having an ion exchange membrane which substantially inhibits permeation of the drug but is water-permeable and a drug layer formed on the body (skin) contacting side of the ion exchange membrane by adhering or depositing the drug by such methods as spray drying and spreading.

4. JP-A-04297277 (Hereinafter Called the Prior Art 4):

(1) The prior art 4 relates to the preceding Japanese patent application filed by this applicant. In FIG. 2, for example, the prior art 4 discloses an iontophoresis electrode section (active electrode section) (in FIG. 2, the negative electrode functions as an active electrode section in relation to the polarity of ions of an ionic drug to be employed) constructed in a multilayer structure of negative electrode plate/gauze with the ionic drug contained therein/cation exchange membrane/gauze with the ionic drug contained therein/anion exchange membrane.

(2) The iontophoresis technology disclosed in the prior art 4 is the technology which has been improved by the present invention, and the limitations of the prior art 4 will be discussed in detail when the present invention is described below.

As to the number of the ion exchange membrane(s) used (arranged) in the iontophoresis electrode section (active electrode section) in each prior art described above, the prior arts 1 through 3 disclose a single layer structure using a single ion exchange membrane, while the prior art 4 discloses a double layer structure using two ion exchange membranes. In this respect, the prior art 4 is different from the other prior arts 1 through 3.

The present invention as will be described in detail below uses a double layer structure like the prior art 4. However, the present invention is based on a technical concept totally different from prior art 4, as it has distinct features that one or more ion exchange membranes are also arranged in the ground electrode section that ion exchange membranes are arranged as many as three or four in total in the iontophoresis device, and, moreover, that both electrode sections have been reconstructed so as to keep the transference number of charged drug ions at a high level and significantly improve the ease (convenience) of handling.

As described above, use of ion exchange membrane(s) has been known in transdermal administration of an ionic drug by iontophoresis.

The above-described conventional iontophoresis technologies using one or more ion exchange membranes, however, lacked a concept or idea of preventing or eliminating various drawbacks associated with an electrochemical reaction on a surface of an electrode plate in the iontophoresis electrode section (active electrode section) and/or the ground electrode section (inactive electrode section).

In other words, the conventional iontophoresis technologies using ion exchange membrane(s) lacked the concept of paying attention to all electrochemical reactions at an iontophoresis electrode section (active electrode) and a ground electrode section (inactive electrode section) and of eliminating drawbacks caused by such reactions in order to establish an iontophoresis technology of higher added value.

In the conventional iontophoresis technologies using ion exchange membrane(s), more specifically, those of the above-described prior arts, one or more ion exchange membranes are used in an active electrode section but no ion exchange membrane is employed in an inactive electrode section, and consequently they have the following drawbacks:

(i) It is difficult to administer an ionic drug (to perform drug delivery) for a long period of time under stably energized conditions (it is difficult to keep it operating for a long period of time at a constant voltage or constant current). For example, physiological saline which is an electrolyte solution (a solution containing an electrolyte substance) is hydrolyzed to produce gas bubbles (oxygen gas, chlorine gas, etc.) on a surface of an electrode plate in an active electrode section of positive (+) polarity, although the polarity of the active electrode section differs depending upon the polarity of charged ions of an active ingredient in an ionic drug. Due to such gas bubbles, the electric resistance increases, resulting in a substantial reduction in the iontophoresis effect (the efficiency of transport of ions) with time. This reduction also takes place by gas bubbles (hydrogen gas and the like) produced at the ground electrode section of negative (−) polarity.

(ii) Burn, inflammation or the like (including electrical burn caused by a current itself or pH-induced burn caused by a sudden change in pH due to $H^+$ or $OH^-$ produced by electrolysis) may occur on the skin at its surface which is in contact with the active electrode section and/or the ground electrode section.

(iii) The skin may be damaged at its surface, which is in contact with an electrode plate [for example☐positive(+) ☐electrode] in the active electrode section, by a harmful substance formed through hydrolysis of sweat on the skin surface and/or physiological saline as an electrolyte solution, for example, by hypochlorous acid (which is known as a strong oxidizing agent) produced based on $Cl^-$ (chlorine ions) and as a result of high acidification (production of HCl).

(iv) The skin may be damaged at its surface, which is in contact with an electrode plate [for example, negative (−) electrode] in the ground electrode section, by a harmful substance formed through hydrolysis of sweat on the skin surface and/or physiological saline as an electrolyte solution, for example, as a result of high alkalinization (production of NaOH).

DISCLOSURE OF THE INVENTION

The present inventors have already made some proposals for solving the above-described drawbacks and limitations of the conventional iontophoresis technologies which use ion exchange membrane(s) (see JP-A-2000-229128), JP-A-2000-237326, and JP-A-2000-237328).

As compared to an iontophoresis electrode section (active electrode section) comprising an iontophoresis electrode plate (active electrode plate) connected to a power source of the same polarity as charged ions of the active ingredient in the ionic drug, as disclosed, for example, in Japanese Language Laid-open Publication (PCT) No. HEI 3-504343 (the prior art 1), an ionic drug arranged on a front side of the iontophoresis electrode plate, and an ion exchange membrane arranged on a front side, that is, on a skin-contacting side of the ionic drug and selective to ions of the same ion species as the charged ions of the active ingredient in the ionic drug, the iontophoresis devices previously proposed by the present inventors as mentioned above are based on the finding that the above-described drawbacks associated with the conventional iontophoresis electrode section (active electrode section) can be solved by adopting the construction between the iontophoresis electrode plate and the ionic drug designed in such ways that, with respect to the iontophoresis electrode plate, (i) an electrolyte solution such as physiological saline is arranged at least on the front side of the iontophoresis electrode plate, and (ii) an ion exchange membrane selective to ions opposite to the charged ions of the active ingredient in the ionic drug is arranged on a front side of the electrolyte solution.

Further, the iontophoresis devices previously proposed by the present inventors as mentioned above are also based on the finding that the above-described drawbacks associated with the conventional ground electrode section (inactive electrode section) can be solved by adopting the construction designed in such ways that, with respect to the electrode plate of the ground electrode section, (iii) an electrolyte solution such as physiological saline is arranged at least on a front side of the ground electrode plate, and (iv) an ion exchange membrane selective to ions opposite to the charged ions of the active ingredient in the ionic drug is arranged on a front side of the electrolyte solution, although it had not been known by that time to arrange an ion exchange membrane on the side of a ground electrode section (inactive electrode section).

However, the iontophoresis devices previously proposed by the present inventors as mentioned above (see JP-A-2000-229128, JP-A-2000-237326, and JP-A-2000-237328) still have room for improvement when they are considered from the viewpoint of efficiency of delivery of an ionic drug into the skin, in other words, from the viewpoint of highly efficient transport (transference number) of the ionic drug and also from the operator's (user's) viewpoint of convenience (maintainability of the device, ease of parts replacement, and handling ease), although they are excellent devices from the viewpoint of avoiding damage to the skin caused by electrochemical reactions at both of the electrode sections (the iontophoresis electrode section and the ground electrode section).

One objective of the present invention is, therefore, to provide an iontophoresis device of high added value, which assures a high transference number in the transdermal delivery of an ionic drug and highly increased convenience, on the basis of the iontophoresis devices previously proposed by the present inventors as mentioned above.

From the above-described viewpoints, the present inventors have conducted a research with a view of providing the iontophoresis devices as having been previously proposed by the present inventors with higher added values. As a result, it has been found that a higher transference number (high transference efficiency of ion species) and better convenience can be assured when:

(1) In the Iontophoresis Electrode Section,
 (1)-1 the electrolyte solution to be arranged on the front side of the electrode plate is formed into a membrane body by using a membrane which has ability of retaining the electrolyte solution in such a state that the membrane is impregnated with the electrolyte solution and also of being electroconductive to ions (conductive to ions) in an electric field, and
 (1)-2 the ionic drug is also formed into a membrane body by using a membrane which has ability of retaining the ionic drug (drug solution) in such a state that the membrane is impregnated with the ionic drug and also of being electroconductive to ions (conductive to ions) in an electric field, and (2) In the Ground Electrode Section,
 (2)-1 the electrolyte solution to be arranged on the front side of the electrode plate is formed into a membrane body by using a membrane which has ability of retaining the electrolyte solution in such a state that the membrane is impregnated with the electrolyte solution and also of being electroconductive to ions (conductive to ions) in an electric field.

The iontophoresis device according to the present invention has been achieved based on the above-described findings.

The present invention can provide an iontophoresis device having high performance (high transference number of ionic drugs), high convenience (maintainability of the device, ease in parts replacement, and handling ease), a compact construction, and high added value.

To describe briefly, the first aspect of the present invention relates to an iontophoresis device useful for administering an ionic drug by iontophoresis, the iontophoresis device having an iontophoresis electrode section (active electrode section) and a ground electrode section (inactive electrode section) both of which are to be connected to a power source, wherein:

(1) The Iontophoresis Electrode Section Comprises:
 (1)-1. an electrode plate connected to a power source of the same polarity as charged ions of the ionic drug,
 (1)-2. an electrolyte-solution-retaining membrane arranged on a front side of the electrode plate and retaining in it an electrolyte solution in such a state that the membrane is impregnated with the electrolyte solution,
 (1)-3. an ion exchange membrane arranged on a front side of the electrolyte-solution-retaining membrane and selective to ions opposite to the charged ions of the ionic drug,
 (1)-4. an ionic-drug-retaining membrane arranged on a front side of the ion exchange membrane and retaining the ionic drug in such a state that the membrane is impregnated with the ionic drug, and
 (1)-5. an ion exchange membrane arranged on a front side of the ionic-drug-retaining membrane and selective to ions of the same ion species as the charged ions of the ionic drug; and (2) The Ground Electrode Section Comprises:
 (2)-1. an electrode plate opposite in polarity to the electrode plate in the iontophoresis electrode section,
 (2)-2. an electrolyte-solution-retaining membrane arranged on a front side of the electrode plate and retaining in it an electrolyte solution in such a state that the membrane is impregnated with the electrolyte solution, and
 (2)-3. an ion exchange membrane arranged on a front side of the electrolyte-solution-retaining membrane and selective to ions opposite to the charged ions of the ionic drug.

The second aspect of the present invention relates to an iontophoresis device, which is a modification of the first aspect of the present invention, wherein:

(2) The Ground Electrode Section Comprises a Cation Exchange Membrane and an Anion Exchange Membrane in Combination, more specifically:
 (2)-1. an electrode plate opposite in polarity to the electrode plate in the iontophoresis electrode section,
 (2)-2. an electrolyte-solution-retaining membrane arranged on a front side of the electrode plate and retaining in it an electrolyte solution in such a state that the membrane is impregnated with the electrolyte solution, and
 (2)-3. an ion exchange membrane arranged on a front side of the electrolyte-solution-retaining membrane and selective to ions of the same ion species as the charged ions of the ionic drug,
 (2)-4. an electrolyte-solution-retaining membrane arranged on a front side of the ion exchange membrane and retaining in it an electrolyte solution in such a state that the membrane is impregnated with the electrolyte solution, and
 (2)-5. an ion exchange membrane arranged on a front side of the electrolyte-solution-retaining membrane and selective to ions opposite to the charged ions of the ionic drug.

In order to improve the performance of the iontophoresis device having the iontophoresis electrode section (active electrode section) and the ground electrode section (inactive electrode section), the present invention features that:

(i) the electrolyte solutions in the iontophoresis electrode section and ground electrode section are formed with solutions containing a readily oxidizable or reducible substance, more specifically, (ii) the electrolyte solutions in the iontophoresis electrode section and ground electrode section are formed with solutions containing ferrous sulfate and ferric sulfate or an organic acid and/or its salt as a readily oxidizable or reducible substance.

To improve the convenience, such as handling ease (user friendliness), of the iontophoresis device, the present invention also relates to a iontophoresis device wherein the elements (members) (1)-1 to (1)-5 or the elements (members) (1)-2 to (1)-5 other than the electrode plate in the iontophoresis electrode section are put together as an integral unit to facilitate replacement of these elements (members), or the elements (members) (2)-1 to (2)-3 or (2)-1 to (2)-5 or the elements (members) (2)-2 to (2)-3 or (2)-2 to (2)-5 other than the electrode plate in the ground electrode section are put together as an integral unit to facilitate replacement of these elements (members).

Other features of the iontophoresis device according to the present invention such as its small size and compact structure will be readily understood by the following description of the technical construction of the present invention.

(Legend)

Figure 1:
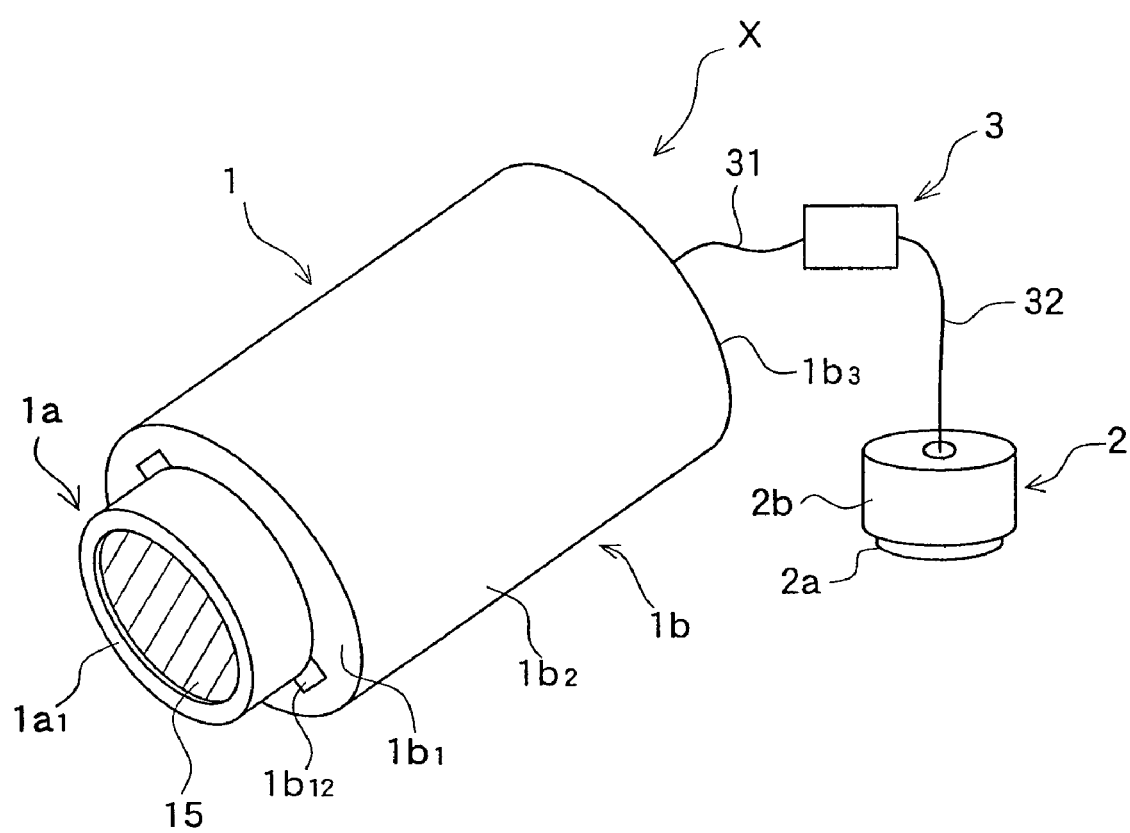
FIG. 1 is a view (overall perspective view) for describing the basic construction of an iontophoresis device (X) according to a first embodiment of the present invention.

X ... Iontophoresis device
1 ... Iontophoresis electrode section
11 ... Electrode plate
12 ... Electrolyte-solution-retaining membrane
13 ... Cation exchange membrane
14 ... Ionic-drug ($As^-Na^+$)-retaining membrane
15 ... Anion exchange membrane
2 ... Ground electrode section
21 ... Electrode plate
22 ... Electrolyte-solution-retaining membrane
23 ... Cation exchange membrane
24 ... Electrolyte-solution-retaining membrane
25 ... Anion exchange membrane
3 ... Power source
31,32 ... Cables
33 ... Conductive spring member
4 ... Skin
A ... Skin-simulating bath
1a ... Small-diameter, cylindrical end section
1b ... Large-diameter, cylindrical grip section

BEST MODES FOR CARRYING OUT THE INVENTION

The following is a detailed description of the technical construction and embodiments of the present invention.

In order to describe the technical construction of the present invention, the drawings will be referred to. Needless to say, it is to be noted that the features shown in the drawings should be interpreted as merely illustrating the embodiments and also that the present invention is by no means limited to those of the drawings.

Figure 2:
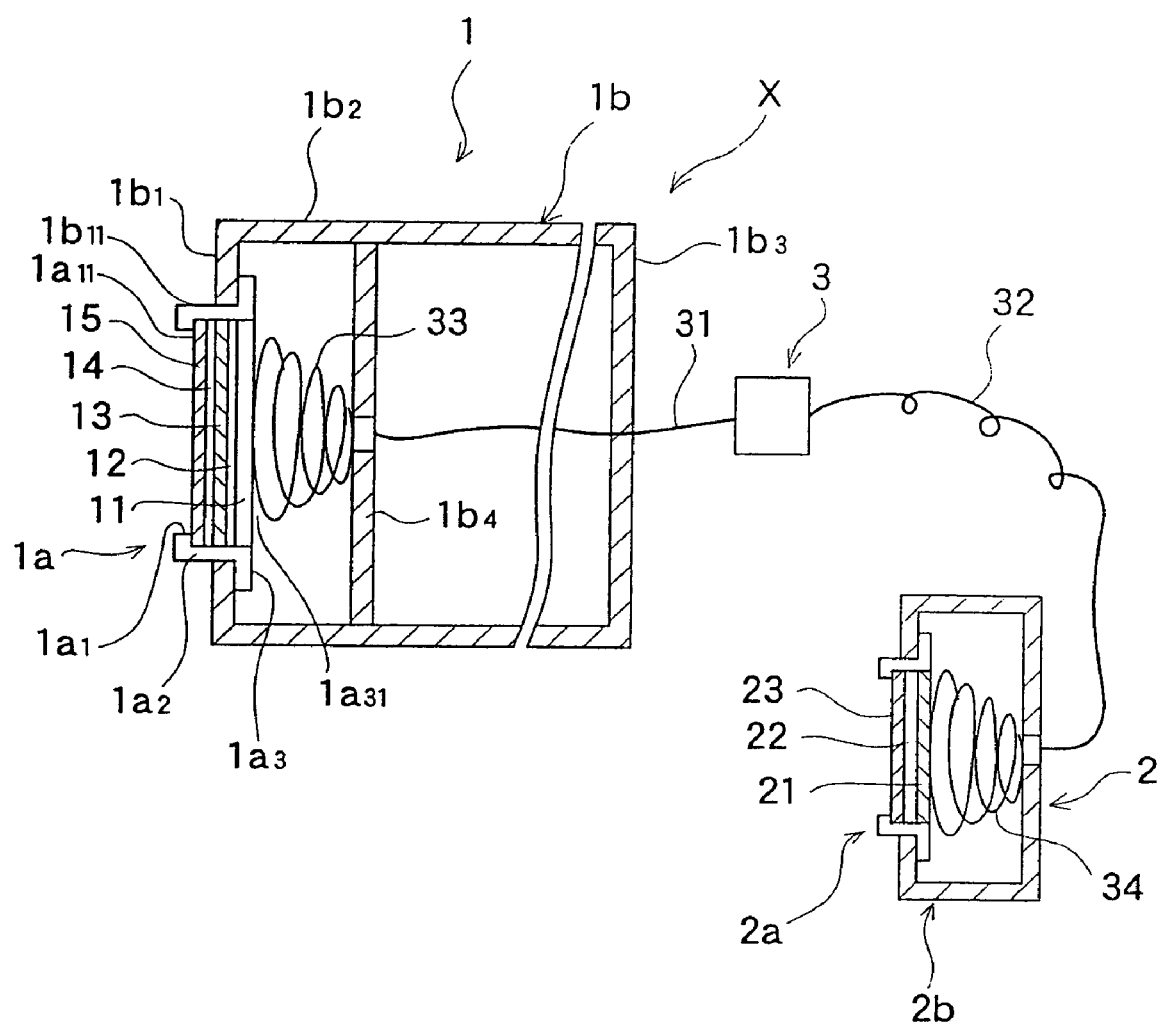
FIG. 2 is a fragmentary cross-sectional view of the iontophoresis device (X) according to the first embodiment of the present invention.
Figure 3:
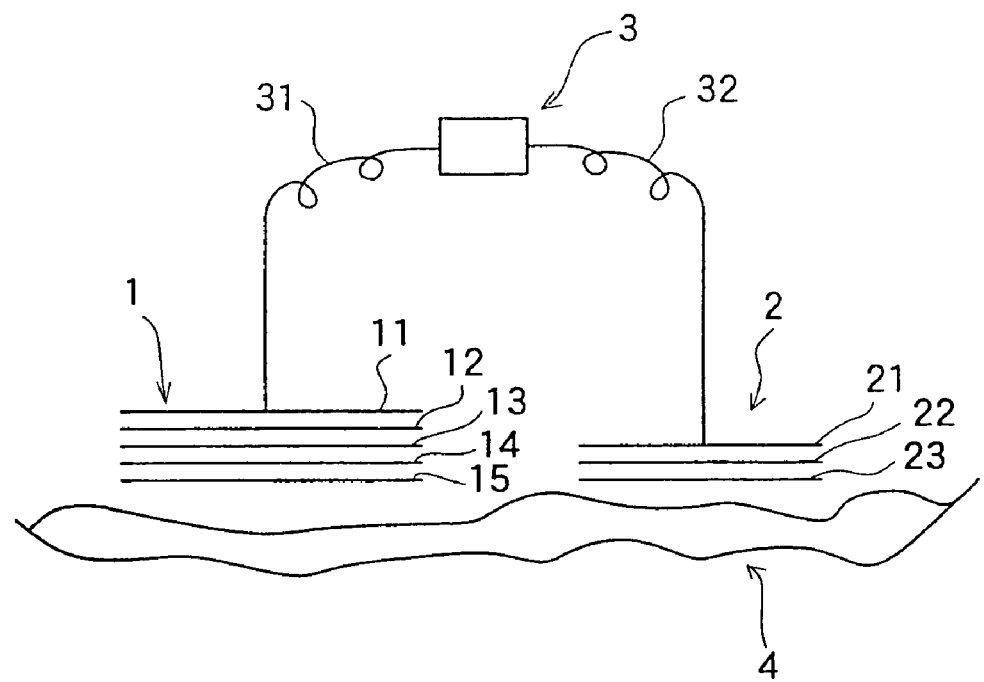
FIG. 3 is a basic construction diagram (fragmentary cross-sectional view) of an iontophoresis electrode section (1) and a ground electrode section (2) in the iontophoresis device (X) according to the first embodiment of the present invention.

FIG. 1 to FIG. 3 are views illustrating the first embodiment of the iontophoresis device (X) according to the present invention.

FIG. 1 is the overall perspective view, while FIG. 2 is the fragmentary cross-sectional view. As shown in these drawings, the iontophoresis device (X) according to the present invention comprises, as main elements (members), an iontophoresis electrode section (1), a ground electrode section (2) and a power source (battery) (3).

FIG. 3 is the basic construction diagram (fragmentary cross-sectional view) of both of the electrode sections, namely, the iontophoresis electrode section (1) and the ground electrode section (2) when administration of an ionic drug is conducted under below-described conditions by the iontophoresis device (X) according to the present invention as illustrated in FIG. 1 and FIG. 2.

The reference numeral (4) in FIG. 3 designates a site of the skin, and FIG. 3 also illustrates an administration method of an ionic drug (drug delivery) by new iontophoresis which can be practiced by the iontophoresis device (X) according to the present invention.

(i) As the ionic drug, the sodium (Na) salt of ascorbic acid (vitamin C), which may hereinafter be abbreviated as $As^-Na^+$, is used. The ionic drug is retained in an impregnatedly-retaining gel membrane (14) in such a state that the gel membrane is impregnated with the ionic drug.

(ii) As the electrolyte solution, a 1:1 mixed aqueous solution of 1 M lactic acid and 1 M sodium fumarate is used. This electrolyte solution is retained in impregnatedly-retaining gel membranes (12,22) in such a state that the gel membranes are impregnated with the electrolyte solution.

(iii) As the types (in terms of ion selective permeability) of employed ion exchange membranes, numerals 13 and 23 designate cation exchange membranes while numeral 15 indicates an anion exchange membrane. These ion exchange membranes are arranged as shown in the drawings.

(iv) An electrode plate (11) in the iontophoresis electrode section (active electrode section) is used as a negative (−) electrode.

(v) An electrode plate (21) in the ground electrode section (inactive electrode section) is used as a positive (+) electrode.

In FIG. 1 to FIG. 3, the reference numerals in these drawings correspond to the reference numerals of the individual elements of the iontophoresis device described above under the Means for Solving the Problems. For example, the element (1)-1 in the iontophoresis device (X) is designated as 11 in the drawings.

Most characteristic features of the iontophoresis device (X) according to the present invention are to provide an iontophoresis device of high added value by increasing the quantity of ions migrated under given electromotive force, the quantity being well known to depend upon the concentration, mobility and valence of ions, because the objective of this type of iontophoresis is to drive (deliver) an ionic drug into the body through the skin (or mucosa) under predetermined electromotive force, in other words, by paying significant attention for the achievement of a high transference number and also by paying attention to the elimination of factors of drawbacks (negative factors) such as electrochemical reactions at the respective electrodes, specifically skin inflammation due to the electrochemical reactions, and further by paying attention for improvements in handling ease and convenience of the device.

In respect of the above-described objective that an ionic drug be driven (delivered) at a high transference number into the body, the prior art cannot be considered to have succeeded. In the present invention, a high transference number (a high efficiency) can be stably achieved with the above-described technical construction as will be described below.

It is also an important objective to eliminate drawbacks such as skin inflammation, which are caused by electrochemical reactions occurring around the electrodes in iontophoresis.

In iontophoresis, electrochemical reactions, specifically certain oxidizing reaction (positive electrode) and reducing reaction (negative electrode) unavoidably occur around the electrodes.

By the above-mentioned electrochemical reactions, formation of a harmful substance through electrolysis of physiological saline as an electrolyte solution (for example, formation of hypochlorous acid from $Cl^-$ at the positive electrode, which is known as a strong oxidizing agent), sudden changes in pH (sudden acidification at the positive electrode, sudden alkalization at the negative electrode) and production of gas bubbles (for example, $H_2$ gas at the negative electrode, $O_2$ gas and $Cl_2$ gas at the positive electrode) occur, for example. These problems lead to serious drawbacks for the practice of iontophoresis, including deleterious effects on the human skin, skin irritations, incapability in energization (due to an increase in resistance as a result of gas production), and the like.

In order to eliminate the drawbacks involved in the conventional administration methods of ionic drugs, such as above-described problems regarding transference number and skin inflammation due to electrochemical reactions, and also to improve the convenience of the device such as its handling ease, the iontophoresis device (X) according to the present invention has adopted, especially as the construction of the respective electrode sections, the construction that the individual elements (members) are constructed into layers as illustrated in FIG. 2 and FIG. 3.

That is to say, the individual elements (members) (11 through 15) of the iontophoresis electrode section (1) and the individual elements (members) (21 through 23) of the ground electrode section (2) are all constructed into layers such as plate members, membrane bodies and ion exchange membranes.

The properties of the membrane bodies, namely, the electrode plates, electrolyte-solution-retaining membranes, ionic-drug-retaining membrane, anion and cation exchange membranes in the present invention are set as described above when $As^-Na^+$ is transdermally delivered as the ionic drug.

The above-described features of the iontophoresis device (X) according to the present invention will hereinafter be described in more detail in the case that sodium ascorbate ($As^-Na^+$) is transdermally delivered as an ionic drug. In this case, charged ions of the active ingredient in the ionic drug are obviously anions ($As^-$).

Therefore, as illustrated in FIG. 3, the electrode plate (11) in the iontophoresis electrode section (1) is a negative (−) electrode while the electrode plate (21) in the ground electrode section (2) is a positive (+) electrode.

Needless to say that, when an ionic drug dissociates into positively charged ions, the polarities of the electrode plates (11,21) and the types (in terms of ion selective permeability) of the ion exchange membranes (13, 15, 23) in the above-described electrode sections are opposite, respectively.

In FIG. 1 through FIG. 3 which illustrate the basic construction of the iontophoresis device (X) according to the first embodiment of the present invention, numeral 1 indicates the iontophoresis electrode section (active electrode section), numeral 2 the ground electrode section (inactive electrode section), numeral 3 the power source, and numeral 4 the skin (or the mucosa).

As shown in FIG. 3, the iontophoresis electrode section (active electrode section)

(1) is constructed of:
  (i) the negative (−) electrode plate (11),
  (ii) the electrolyte-solution-retaining membrane (12) with the electrolyte solution (1 M lactic acid/1 M sodium fumarate) retained therein in such a state that the membrane is impregnated with the electrolyte solution,
  (iii) the cation exchange membrane (13),
  (iv) the ionic-drug-retaining membrane (14), and
  (v) the anion exchange membrane (15).

As also illustrated in FIG. 3, the ground electrode section (2) is constructed of:
  (i) the positive (+) electrode plate (21),
  (ii) the electrolyte-solution-retaining membrane (22) with the electrolyte solution (1 M lactic acid/1 M sodium fumarate) retained therein in such a state that the membrane is impregnated with the electrolyte solution, and
  (iii) the cation exchange membrane (23).

In the present invention, the electrolyte-solution-retaining membranes (12,22) in both of the electrode sections (1,2) are not limited to those impregnated with the above-mentioned electrolyte solution composed of 1 M lactic acid and 1 M sodium fumarate as an electrolyte solution. They may also be made of those impregnated using physiological saline (for example, 0.9% aqueous solution of NaCl) or those impregnated with a compound, which has an oxidation-reduction potential lower than the oxidation-reduction potential of water and can be more readily oxidized or reduced compared with the electrolytic reaction of water (oxidizing and reducing reactions of water), as an electrolyte solution.

In the present invention, the electrolyte-solution-retaining membranes (12,22) in both of the electrode sections (1,2) may also be made of membranes retaining an ionic drug (for example, $As^-Na^+$ as mentioned above) as a readily oxidizable or reducible compound in such a state that the membranes are impregnated with the ionic drug, because, as an electrolyte solution, the oxidation-reduction potential of the ionic drug is generally lower than that of water. As such, ionic drugs are oxidized or reduced prior to the hydrolysis of water, the drawback associated with the hydrolysis of water can be eliminated.

Next, with reference to the basic construction diagrams (FIG. 1 to FIG. 3) of the iontophoresis device (X) according to the present invention, the construction of a more specific iontophoresis device (X) for practicing the new administration method of an ionic drug will be described in the order of the specific construction of the iontophoresis electrode section (active electrode section) (1) and the specific construction of the ground electrode section (inactive electrode section) (2).

In the iontophoresis device (X) according to the present invention, the electrode plate (11) in the iontophoresis electrode section (active electrode section) (1) can be composed of a desired electrode plate. Further, the electrode plate (21) in the ground electrode section (inactive electrode section) (2) can also be composed of a desired electrode plate.

For example, they can be composed of inert electrodes made of a conductive material such as carbon or platinum. Commercially-available, patch-type Red Dot™ monitoring electrodes (products of 3M Health Care Limited), which were used upon investigating possible reactions of the skin at both of the electrode sections (1,2) by using the iontophoresis device according to the present invention as will be described subsequently, are also useful.

In the iontophoresis device (X) according to the present invention, active electrodes known in the field of iontophoresis may also be adopted as the electrode plates (11,21) instead of the above-described inert electrodes. When an active ingredient of an ionic drug becomes positive (+) ions, specifically when morphine hydrochloride or lithium chloride is used as an ionic drug (in this case, morphine ions or lithium ions as a drug ingredient are positive ions, and chlorine as counter ions are negative ions), illustrative of the above-mentioned active electrodes are silver electrodes which react as positive (+) plates with these counter ions.

In the case of the above-described active electrodes, the silver electrode readily reacts with chlorine ions ($Cl^-$) so that insoluble AgCl is formed in accordance with the formula: $Ag + Cl^- \rightarrow AgCl + e^-$. An advantage available from the use of the above-described active electrodes resides in that the electrolytic reaction of water can be prevented because the standard potential of the above reaction is lower than the standard potential of the electrolytic reaction of water at the positive (+) electrode. It is, hence, possible to avoid sudden acidification based on $H^+$ ions at the anode (positive electrode) and also sudden alkalization based on $OH^-$ ions at the cathode (negative electrode).

In the iontophoresis device (X) according to the present invention, however, because plural, at least, three ion exchange membranes different in ion selective permeability are used in the iontophoresis system as described above and an insoluble substance (insoluble fine particles) such as silver chloride (AgCl) formed at the active electrode may impair the properties of the ion exchange membranes in some instances, the care must be taken in their use.

As the iontophoresis device (X) according to the present invention uses the plural ion exchange membranes different in ion selective permeability, it is preferred for the reason mentioned above to use inert electrodes instead of using more costly special electrodes such as active electrodes.

The electrolyte-solution-retaining membrane (12) in the iontophoresis electrode section (1) in the present invention is composed of a thin membrane body with an electrolyte solution retained therein in such a state that the membrane is impregnated with the electrolyte solution. As this thin membrane body is of the same kind as a thin membrane body employed as the below-described ionic-drug-retaining membrane with an ionic drug retained therein in such a state that the membrane is impregnated with the ionic drug and therefore, its details will be described subsequently.

As the electrolyte solution, any desired electrolyte solution can be used. However, those which may cause trouble on the human skin through electrode reactions should be avoided.

For electrolyte solutions suitable in the present invention, organic acids and their salts, which exist in the human metabolic cycle, are preferred from the viewpoint of harmlessness to the body.

For example, lactic acid, fumaric acid and the like are preferred. Specifically, an aqueous solution of 1 M lactic acid and 1 M sodium fumarate (Na salt) at a ratio of 1:1 is preferred. This electrolyte solution is soluble relatively well in water, and allows a current to flow well through it. When a current is caused to flow as a constant current, its electrical resistance is low, and no substantial pH change takes place at the electrodes.

Examples of other electrolytes include:

(1) physiological saline (0.9% aqueous solution of NaCl), and (2) a mixed aqueous solution of ferrous sulfate ($FeSO_4$) and ferric sulfate [$Fe_2(SO_4)_3$] (0.2 M:0.2 M equiratio aqueous solution).

In the case of the physiological saline, gas bubbles may be produced at both of the negative and positive electrodes and may act as a resistance to inhibit a constant-current power supply device as an accessory to the iontophoresis device (X), although the physiological saline has high conductivity. Further, since chlorine gas is produced from the positive electrode so that the solution tends to become acidic (formation of HCl), full measures must, therefore, be taken to avoid damage to the skin.

In the case of the mixed aqueous solution of ferrous sulfate ($FeSO_4$) and ferric sulfate [$Fe_2(SO_4)_3$], there are merits in that, when a current is applied, resistance is low and occurrence of gas bubbles at the electrodes is prevented, for reasons to be mentioned subsequently herein.

In such a case, to cope with a potential problem that the electrolyte solution may leak out in the course of manufacture of the iontophoresis device (X), it is necessary to take sufficient countermeasures, for example, in connection with the corrosion resistance of the device, negative (undesirable) effects of sulfuric acid (deleterious substance) on the human body (skin).

The electrolyte solution kept in contact with the negative (−) electrode plate (11) in the iontophoresis electrode section (1) in the present invention may preferably be composed of one including a readily reducible compound.

On the other hand, the electrolyte solution kept in contact with the positive (+) electrode plate (21) in the ground electrode section (2) according to the present invention may preferably be composed of one including a readily oxidizable compound.

Needless to say, the positions of arrangement of the electrolyte solutions, in which the readily oxidizable compound and the readily reducible compound are added, respectively, should be set corresponding to the electrochemical reactions at the respective electrode plates, namely, the reducing reaction at the negative (−) electrode and the oxidizing reaction at the positive (+) electrode.

In the present invention, the readily oxidizable and reducible compounds added to the electrolyte solutions, respectively, are preferably those excellent in biosafety, economy (low price and good availability), etc. Illustrative are inorganic compounds such as ferrous sulfate and ferric sulfate; medicaments such as ascorbic acid (vitamin C) and sodium ascorbate; acidic compounds existing on the skin, such as lactic acid; and organic acids such as oxalic acid, malic acid, succinic acid and fumaric acid and/or salts thereof.

As is appreciated from the foregoing, the above-described equiratio aqueous solution of 1 M lactic acid and 1 M sodium fumarate is preferred as the electrolyte solutions.

In the case of a compound which is more readily oxidizable or reducible than the hydrolytic reaction of water (oxidation at the positive electrode and reduction at the negative electrode), for example, in the case of ferric sulfate, ferric ions are readily reduced into ferrous ions at the negative electrode. In the case of ferrous sulfate, on the other hand, ferrous ions are readily oxidized into ferric ions at the positive electrode.

As a consequence, the drawbacks associated with the hydrolytic reaction of water can be eliminated. Coupled with the specific embodiments of arrangement of the ion exchange membranes in the present invention, the iontophoresis device (X) having excellent performance is provided.

A detailed description will now be made about the merits available from the use of electrolyte solutions containing a readily oxidizable compound or a readily reducible compound, respectively, as the electrolyte solutions.

In the iontophoresis electrode section (1) and ground electrode section (2), electrochemical reactions take place so that the electrolyte solutions undergo dissociation. As a result, gas bubbles are produced in both of the electrode sections (1,2) so that the electrode plates and their corresponding electrolyte solutions are prevented from contacting with each other. For example, $H_2$ gas is produced at the negative electrode, and $Cl_2$ and $O_2$ gases are produced at the positive electrode.

If such a situation arises, the electric resistances of the electrode plates (11,21) increase for the gas bubbles so that no current is allowed to flow no matter how much a voltage is raised. In the case of the above-described transdermal delivery of $As^-Na^+$, it is impossible to stably energize for a long time (30 minutes or longer). This is an extremely serious problem from the viewpoint of practical utility of the iontophoresis device (X).

To stably perform iontophoresis by eliminating the above-described instability factor, it is extremely important to inhibit production of gas bubbles in the electrode plates (11, 21).

To achieve this purpose, it is useful to add a substance, which is susceptible to an oxidizing or reducing reaction without producing gas bubbles, to both of the electrolyte solutions.

Described specifically, oxygen or hydrogen is produced when water is oxidized or reduced. To inhibit these reactions, ferrous sulfate, ferric sulfate, ascorbic acid or the sodium salt thereof is added as an example to the electrode compartment solutions (electrolyte solutions). When sodium ascorbate is used, for example, sodium ascorbate is oxidatively decomposed at the positive (+) electrode, where an oxidizing reaction takes place, instead of production of oxygen. At the negative (−) electrode where a reducing reaction takes place, on the other hand, sodium ascorbate is reductively decomposed instead of occurrence of hydrogen. As a consequence, it is possible to inhibit production of oxygen or hydrogen gas bubbles which impair the stability of energization characteristics.

By sacrificially using a substance which is more readily oxidizable or reducible than water in an electrochemical reaction (a substance having an oxidation-reduction potential lower than the oxidation-reduction potential of water) such as sodium ascorbate as described above, the production of gas bubbles in both of the electrode sections (1,2) can be inhibited so that the iontophoresis device (X) can perform more stable operation.

In addition to the above-described ferrous sulfate, ferric sulfate and ascorbic acid, any substance can obviously be used as the sacrificial substance in the present invention insofar as it undergoes oxidation or reduction and inhibits the electrolytic reaction of water.

When sodium ascorbate is used as the sacrificial substance, sodium ascorbate changes into:

(i) $CO_2$, $H_2CO_3$ and the like at the electrode (negative electrode) where a reducing reaction takes place, and (ii) dehydroascorbic acid, 2,3-diketo-D-gulonic acid and the like at the electrode (positive electrode) where an oxidizing reaction takes place.

The iontophoresis electrode section (1) in the present invention makes the combined use of the cation exchange membrane (13) and the anion exchange membrane (15) as illustrated in FIG. 3.

As the cation exchange membrane (13) selective to ions opposite to the ion species ($As^-$) of the active ingredient in the iontophoretic drug ($As^-Na^+$) in the present invention, it is possible to use NEOSEPTA (CM-1, CM-2, CMX, CMS, CMB or the like) (product of TOKUYAMA CORPORATION).

As the anion exchange membrane (15) selective to ions of the same type as the ion species ($As^-$) of the active ingredient in the ionic drug ($As^-Na^+$) in the present invention, it is possible to use NEOSEPTA (AM-1, AM-3, AMX, AHA, ACH, ACS, ACS-3 or the like) (product of TOKUYAMA CORPORATION).

The ionic drug ($As^-Na^+$) retaining membrane (14) in the iontophoresis electrode section (1) in the present invention is composed of a thin membrane body with the ionic drug retained therein in such a state that the membrane body is impregnated with the ionic drug.

In addition to sodium ascorbate ($As^-Na^+$) described above, conventionally known ionic drugs are usable in the present invention as the ionic drug without any limitations. Typical examples of this type of ionic drugs are as mentioned above.

In the present invention, (1) the electrolyte-solution-retaining membrane (12) and (2) the ionic-drug-retaining membrane (14)

are composed of thin membrane bodies with an electrolyte solution and an ionic drug retained therein, respectively, in such a state that the thin membrane bodies are impregnated with the electrolyte solution and the ionic drug, respectively. As the thin membrane bodies, those of the same kind or of different kind can be selected for combined use from thin membrane bodies to be described subsequently herein.

The thin membrane bodies will hereinafter be described in detail.

For the iontophoresis device (X), there are operation conditions (current value, voltage value) set from the viewpoint of safety to the human skin. The most important question, therefore, is how to achieve efficient transport of an ionic drug into the skin (transdermal delivery), that is, to obtain a high transference number under the conditions which assure the safety. From this viewpoint, a description will be made about the thin membrane body, especially properties of the ionic-drug-retaining membrane (14). In the present invention, for the thin membrane bodies for the electrolyte-solution-retaining membrane (12) in the iontophoresis electrode section (1) and the electrolyte-solution-retaining membranes (22,24) in the below-described ground electrode section (2), the same kind of the thin membrane body as that which makes up the ionic-drug-retaining membrane (14) is used.

In general, iontophoresis (transdermal delivery) is performed under constant current conditions or constant voltage conditions. A description will hereinafter be made from the viewpoint of performing iontophoresis under constant current conditions, but the present invention is not limited to iontophoresis under such constant current conditions.

In the present invention, operation conditions with the above-mentioned safety of the iontophoresis device (X) taken into consideration comprise:

(1) constant current conditions, specifically 0.1 to 0.5 mA, preferably 0.1 to 0.3 mA, and (2) voltage conditions which are suited to establish the above-described constant current and are safe, specifically below 50 V, preferably below 30 V.

In order to efficiently deliver the ionic drug under the above-described conditions, it is important for the thin membrane bodies to have sufficient ability to retain the ionic drug in such a state that the thin membrane bodies are impregnated with the ionic drug and also to have sufficient ability to cause the impregnatedly retaining ionic drug to move toward the skin under the above-described electric field conditions, in other words, ability to cause ion species of the impregnatedly retaining ionic drug to move toward the skin, and in still other words, ion-electroconductive (ion-conductive) ability.

Under the above-described constant current conditions, the ionic-drug-retaining membrane (thin membrane body) in the present invention should be equipped with desired impregnatedly-retaining ability for the ionic drug and also with ability to cause ion species of a desired active ingredient to move toward the skin (hereinafter called ion electroconductivity or ion conductivity).

As a result of many experiments, the present inventors found that a high transference number (high drug-delivering ability) as great as 70 to 80%, for example, can be obtained when the degree of impregnation of the ionic-drug-retaining membrane (14) with a solution of the ionic drug is in a range of 30 to 40% in the layered construction of the membrane bodies in the iontophoresis electrode section (1), in other words, in the three-layer structure of the cation exchange membrane (13), the ionic-drug-retaining membrane (14) and the anion exchange membrane (15).

The above-described degree of impregnation of 30 to 40% is a value extremely close to the content of water in the cornea of the human eyeball. They are, hence, in a surprising correlation.

Further, the above-described transference number of 70 to 80% is a value of an extremely high level compared with those available from the conventional iontophoresis technologies.

Incidentally, the measurement of a degree of impregnation should be conducted immediately after impregnation to avoid time-dependent influence. Likewise, the measurement of a transference number should be conducted by arranging the ionic-drug-retaining membrane, which has been impregnated with the ionic drug, between the ion exchange membranes (13) and (15) while concurrently assembling the other members such that time-dependent changes can be avoided as much as possible.

It should be noted that the above-described degree of impregnation with the solution of the ionic drug and the transference number of the ionic drug are used as indexes in the present invention. These are because no index for objectively and totally evaluating the ability of the thin membrane body to be impregnated with the ionic drug, the ability of the thin membrane to retain the ionic drug and the ability of the thin membrane body to make ion species of the active ingredient in the ionic drug, which is retained in the thin membrane body in such a state that the thin membrane body is impregnated with the ionic drug, to move toward the skin (ability of ion electroconductivity or ion conductivity).

As other indexes which can be used as substitutes for the degree of impregnation and the transference number as indexes of the properties of the thin membrane body (the impregnatability, the retaining ability and the ion conductivity), there are microporosity and transference number.

As the ionic-drug-retaining membrane (14) for use in the present invention, a hydrogel body of acrylic resin (acrylic hydrogel membrane) can be exemplified for its high biosafety, as typified by the use of the acrylic resin as contact lenses.

This acrylic hydrogel membrane is a gel body (of an intermediate form between liquid and solid) having a three-dimensional network structure (crosslinked structure), and a mixture obtained by adding water as a dispersant and an electrolyte substance (NaCl or the like) to the acrylic hydrogel membrane allows a current to flow through it as a result of migration of dissociated ions of the electrolyte substance. In other words, the mixture obtained by impregnating the acrylic hydrogel membrane (which can be considered to be a microporous gel membrane) with an aqueous solution of the electrolyte substance can be considered to become a high-molecular adhesive material equipped with ion conductivity (ion electroconductivity). This is because the acrylic hydrogel membrane becomes conductive to ions (electroconductive to ions) as a result of penetration of the dispersing medium and dissociated ion species into the three-dimensional network of high-molecular chains in the acrylic hydrogel membrane and migration of the ion species through the network structure in an electrical field.

The above-described correlation between the degree of impregnation of the acrylic hydrogel membrane and the transference number can be easily adjusted by controlling the size of the three-dimensional network structure and the kinds and proportions of monomers making up the resin.

In the present invention, an acrylic hydrogel membrane having a degree of impregnation of 30 to 40% and a transference number of 70 to 80% can be prepared from 2-hydroxyethyl methacrylate and ethylene glycol dimethacrylate (monomer ratio: 98-99.5 to 0.5-2). Such acrylic hydrogel membranes (microporous gel membranes) are available, for example, from Sun Contact Lens Co., Ltd. In the present invention, the degree of impregnation and the transference number have been confirmed to be substantially the same within the usual thickness range of the acrylic hydrogel membrane (microporous gel membrane) for use in the present invention, that is, in a range of from 0.1 mm to 1.0 mm.

As another ionic-drug-retaining membrane (14) for use in the present invention, there is a segmented polyurethane gel membrane (GELLODE™, product of Takiron Co., Ltd.).

This membrane is a segmented polyurethane gel membrane, which contains polyethylene glycol (PEG) and polypropylene glycol (PPG) as segments and has been produced from these monomers and diisocyanate.

The segmented polyurethane gel membrane has a three-dimensional structure crosslinked by urethane bonds, and its degree of impregnation, transference number and adhesive force can be easily adjusted by controlling the size of openings in the network and the proportions of the monomers, as in the case of the above-described acrylic hydrogel membrane.

In the segmented polyurethane gel membrane (microporous gel membrane) added with water as a dispersion medium and an electrolyte substance (an alkali metal salt or the like), oxygen atoms of ether bonds in a segment-forming polyether and the alkali metal salt forms a complex and, when electricity is applied, an ion of the metal salt moves to the oxygen in the next void ether bond so that conductivity (ion electroconductivity) is exhibited. Incidentally, the segmented polyurethane gel membrane (microporous gel membrane) is used as a gel pad for ultrasonic diagnostics by making use of its conductive (ion electroconductive) property.

The segmented polyurethane gel membrane (microporous gel membrane) is free of irritation to the skin and is a substance having high safety, because use of PEG-PPG-PEG copolymer, which make up the segments, as a cosmetic ingredient has been approved.

As another ionic-drug-retaining membrane (14) for use in the present invention, an ion-conductive microporous sheet for the formation of a gel-like solid electrolyte, for example, as a gel-like solid electrolyte sheet in a solid cell (secondary cell) is useful.

Ion-conductive microporous sheets of this type are disclosed, for example, in JP-A-11273452, and are basically formed of a microporous polymer having a porosity of from 20 to 80% and composed primarily of an acrylonitrile polymer.

More specifically, the microporous polymer is an acrylonitrile copolymer composed of 50 mole % or more (preferably 70 to 98 mole %) of acrylonitrile and having a porosity of from 20 to 80%.

The acrylonitrile-based, gel-like solid electrolyte sheet (solid cell) is prepared by impregnating an acrylonitrile-based copolymer sheet, which is soluble in a non-aqueous solvent and has a porosity of 20 to 80%, with an electrolyte-containing non-aqueous solvent to form the copolymer sheet into a gel. Gel bodies include gel-like bodies and hard membrane-like bodies.

From the viewpoints of ion conductivity, safety and the like, the acrylonitrile-based copolymer sheet soluble in the non-aqueous solvent can preferably be composed of an acrylonitrile/$C_1$-$C_4$ alkyl (meth)acrylate copolymer, acrylonitrile/vinyl acetate copolymer, acrylonitrile/styrene copolymer, acrylonitrile/vinylidene chloride copolymer or the like. To form the copolymer sheet into a microporous sheet, conventional processes can be adopted including the wet (dry) paper making process, the needle punching process as a production process of non-woven fabric, the water jet process, and formation of a melt-extruded sheet into a microporous body by stretching or solvent extraction.

Among the ion-conductive microporous sheets of acrylonitrile-based copolymers employed in solid cells, gel bodies (including gel-like bodies and hard membrane bodies) each of which retains an ionic drug in a three-dimensional network of polymer chains and can achieve the above-described degree of impregnation and transference number are useful as thin membrane bodies, and each of which can serve as a base for the ionic-drug-retaining membrane (14) in the present invention.

As to conditions under which the above-described thin membrane body (microporous gel membrane) is impregnated with the ionic drug or the electrolyte solution in the present invention, optimal conditions can be determined from the viewpoint of a degree of impregnation, an impregnation speed and the like. For example, impregnation conditions of 40☐ and 30 minutes may be chosen.

In the present invention, various thin membrane bodies each of which is useful as a base for the ionic-drug-retaining membrane (14) can be used for the thin membrane body which serves as a base for the electrolyte retaining membrane (12). These thin membrane bodies permit, in an electrical field efficient migration of ion species dissociated in the electrolyte solution with which the membrane body is impregnated.

Owing to the above-described technical construction of the iontophoresis electrode section (1) of the iontophoresis device (X) according to the present invention, as compared to the transdermal delivery by conventional iontophoresis devices, the ionic drug can be transdermally delivered stably over a longer period of time at a higher transference number, and higher biosafety can be obtained.

Described specifically, owing to the above-described technical construction of the iontophoresis electrode section (1), stable energization properties can be obtained over a long period of time. In other words, the ionic drug can be efficiently delivered into the body stably for a long period of time through the skin (4) (drug delivery). It is also possible to prevent formation of a harmful substance through electrolysis in the electrode section, that is, to achieve a high level of biosafety.

Next, with reference to FIG. 3, the construction of the ground electrode section [positive (+) electrode] (2) of the iontophoresis device (X) according to the present invention will be described.

Up to the present, no iontophoresis technology which realizes stable energization properties and biosafety has been proposed. This is probably because the conventional technologies of iontophoresis were developed under a simplistic concept of the construction of the ground electrode section that it is arranged merely to establish grounding.

This observation is affirmed in view of Japanese Language Laid-open Publication (PCT) No. HEI 3-504343, JP-A-03094771 and JP-A-04197277 to which this application is related, which were described above under Background Art.

In addition to the above-described construction of the iontophoresis electrode section (1) in the iontophoresis device (X), the present invention has also adopted, in relation to the overall construction of the device, a novel technical construction for the ground electrode section (2), which is different from the conventional technical construction, from the viewpoint of permitting stable administration of an ionic drug for a long period of time at a high transference number (high efficiency) by iontophoresis and also obtaining a high level of biosafety.

As shown in FIG. 3, the ground electrode section (2) of the iontophoresis device (X) according to the present invention is constructed of the electrode plate (21) of a polarity opposite to the electrode plate (11) in the iontophoresis electrode section (1), the electrolyte-solution-retaining membrane (22) arranged on the front side of the electrode plate (21), and the ion exchange membrane (23) arranged on the front side of the electrolyte-solution-retaining membrane (22), that is, on the side of the skin (4) and selective to ions opposite to charged ions of the ionic drug.

It is a significant characteristic feature unseen in the prior art that in the iontophoresis device (X) according to the present invention, the ion exchange membrane (23) is indispensably arranged in the ground electrode section (2) so as to heighten biosafety.

In the iontophoresis device (X) according to the present invention, the electrolyte solution in the electrolyte-solution-retaining membrane (22) of the ground electrode section (2) may be composed of one containing a substance, the oxidation-reduction potential of which is lower than the oxidation-reduction potential of water, like the above-described electrolyte solution in the electrolyte-solution-retaining membrane (12) of the iontophoresis electrode section (1), from the viewpoint of biosafety and stable operation for a long period of time. It is also a significant feature that the iontophoresis device (X) is provided with high added value by arranging the ion exchange membrane (23) in the ground electrode section (2) and also by forming the electrolyte solution with the above-described readily oxidizable or reducible substance added therein.

As depicted in FIG. 3, in the first embodiment of the present invention, when an active ingredient of an ionic drug such as sodium ascorbate ($As^-Na^+$) is charged to negative (−), the electrode plate (21) in the ground electrode section (2) of the iontophoresis device (X) becomes positive (+), the electrolyte solution in the electrolyte-solution-retaining membrane (22) is composed of same 1:1 mixed aqueous solution of 1M lactic acid and 1 M sodium fumarate as in the iontophoresis electrode section (1), and the ion exchange membrane (23) is composed of a cation exchange membrane.

In the present invention, the electrolyte solution in the electrolyte-solution-retaining membrane (22) of the ground electrode section (2) can be composed of physiological saline which as mentioned above, contains a readily oxidizable or reducible substance, for example, ferric sulfate, ferric sulfate containing ferrous sulfate (an equimolar solution of both sulfates), ascorbic acid or sodium ascorbate.

The administration method of the ionic drug by iontophoresis, which was explained with reference to the iontophoresis device (X) shown in FIG. 3, was in the case of sodium ascorbate ($As^-Na^+$) that the active ingredient of the ionic drug is charged negative (−) as described above.

Even when the active ingredient of an ionic drug is charged positive (+), it can be administered likewise in the present invention.

Examples of ionic drugs of this type whose active ingredients are charged positive (+) include procaine hydrochloride and lidocaine hydrochloride as local anesthetic drugs.

The polarities of the individual electrode plates (11,21) and the ion exchange properties of the ion exchange membranes (13,15,23) must be made opposite in this case to the corresponding polarities and ion exchange properties in the above-described case in which sodium ascorbate ($As^-Na^+$) was administered.

When an ionic drug chargeable positive (+) is used as described above, the features of the present invention can be easily understood by making an inference from the above-described case in which sodium ascorbate chargeable negative (−) was administered.

As the above-described power source (3) shown in FIG. 1 to FIG. 3, any power source can be used as desired in the present invention.

In the present invention, a cell, a constant-voltage generator, a constant-current generator (galvanostat), a constant-voltage and constant-current generator, or the like can be used as the power source (3).

Figure 4:
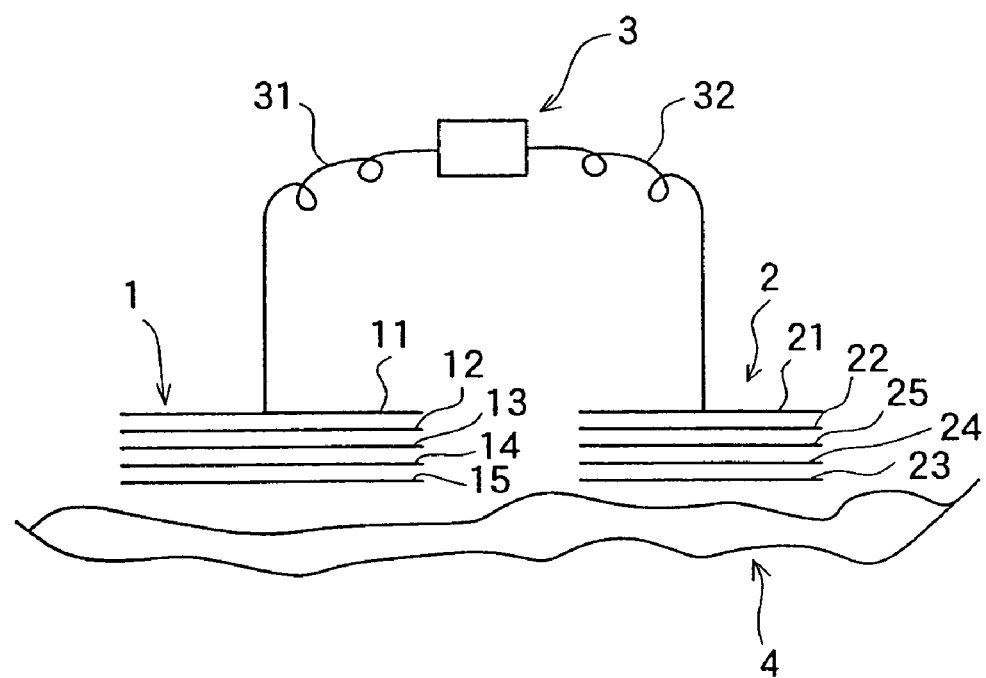
FIG. 4 is a diagram illustrating a modification of the iontophoresis device (X) shown in FIG. 3, specifically a modification of the ground electrode section (2)

FIG. 4 shows the modification of the iontophoresis device (X) according to the first embodiment illustrated in FIG. 3, which specifically uses two ion exchange membranes, i.e., a cation exchange membrane (23) and an anion exchange membrane (25) on the side of a ground electrode section (2).

In FIG. 4, reference numeral (24) indicates an electrolyte-solution-retaining membrane which is similar to the electrolyte-solution-retaining membrane (22) in the ground electrode section (2) depicted in FIG. 3.

The modification illustrated in FIG. 4 is effective in preventing the skin troubles which may otherwise occur through the electrochemical reaction on the side of the ground electrode section (2). Owing to the arrangement of the ion exchange membranes as illustrated in FIG. 4, specifically owing to the embodiment that the two ion exchange membranes (13,15) of different types are arranged on the side of the iontophoresis electrode section (1) and the two ion exchange membranes (23,25) of different types are arranged on the side of the ground electrode section (2), only $As^-$ are fed to the human skin (4) from the side of the iontophoresis electrode section (1), only $Na^+$ are fed from the side of the ground electrode (2), and no other substances are practically fed. This modification, therefore, has extremely high biosafety.

EXAMPLES

<Experiment by Equivalent Experimenting Equipment>

Next, a description will be made on an experiment in which sodium ascorbate ($As^-Na^+$) was experimentally administered as an ionic drug by using experimental equipment equivalent to the basic construction diagram of the iontophoresis device (X) as illustrated in FIG. 4.

By experiments and comparative experiments to be described subsequently herein, it will be appreciated that the iontophoresis device (X) according to the present invention can transdermally deliver an ionic drug at an extremely high transference number or at high efficiency.

1. Experimenting Equipment

Figure 5:
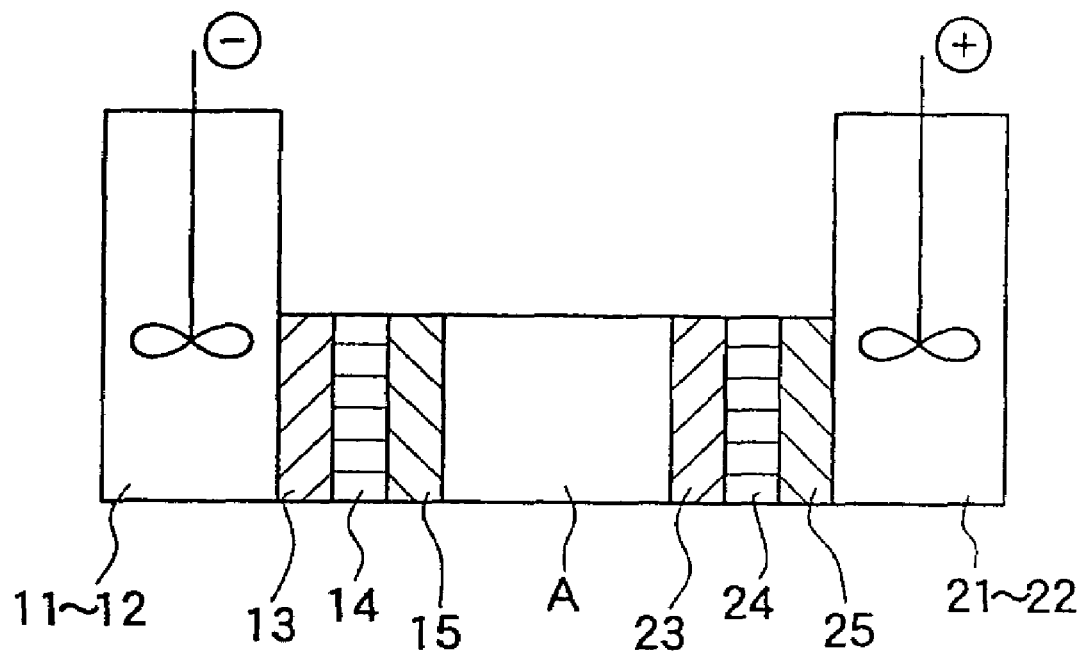
FIG. 5 is a diagram illustrating experimenting equipment equivalent to the device (X) according to the first embodiment of the present invention.

FIG. 5 is the schematic diagram of the experimenting equipment equivalent to the iontophoresis device (X) shown in FIG. 4.

The reference numerals and letter of the experimenting equipment will be explained as follows:

(1) Reference numerals 11, 12, 13, 14, 15, 21, 22, 23, 24 and 25 are the same as in FIG. 3 to FIG. 4.

(2) The elements (11-12) in the iontophoresis electrode section (1) and the elements (21-22) in the ground electrode section (2) were constructed by using platinum plates as the electrode plates, using a 1:1 aqueous solution of 1 M lactic acid and 1 M sodium fumarate as an electrolyte solution in both of the iontophoresis electrode section (1) and ground electrode section (2) and making the electrolyte solution stirrable.

(3) As the cation exchange membranes (13,23) and anion exchange membranes (15,25), NEOSEPTA CMS (cation) and NEOSEPTA AMX (anion) (products of TOKUYAMA CORPORATION) were used, respectively.

(4) As a thin membrane body for the ionic-drug-retaining membrane designated at reference numeral (14), the above-described acrylic hydrogel membrane (product of Sun Contact Lens Co., Ltd.) was used.

(5) As a thin membrane body for the electrolyte-solution-retaining membrane designated at reference numeral (24), the above-described acrylic hydrogel membrane (product of Sun Contact Lens Co., Ltd.) was used, and as the electrolyte solution, a 0.9% aqueous solution of NaCl was used.

(6) Reference letter A designates a skin-simulating bath (chamber) which simulates the skin, and that bath was filled with a 0.9% aqueous solution of NaCl.

Upon conducting an experiment, the elements (13 to 15) in the iontophoresis electrode section (1) and the elements (23 to 25) in the ground electrode section (2) were put into integral structures, respectively, and assembled in the experiment equipment. In the present invention, the above-described formation of the members into the integral structures can be effected by a conductive adhesive, heat sealing or the like.

2. Experimenting Conditions

1) Current value (constant current): 0.3 mA

2) Variations in voltage value (from the initial constant voltage values 30V): 0.8 to 1.2 V
3) Energized time: 15 minutes to 35 minutes 3. Experimental Results and Discussion The amount (micron mol) of ascorbic acid in the skin-simulating bath (A) subsequent to each predetermined energized time was investigated.

The results are presented below in Table 1.

1) It is appreciated from Table 1 that the amount of ascorbic acid that reached the skin-simulating bath (A) increased with the energized time.

2) After energization at 0.3 mA for 35 minutes, the percent transference was found to be extremely high, that is, 80%.

(Note) The term transference number means a Hittorf number, and which indicates the percentage of a current of specific ions, which is determined based on movement of specific ions, based on the whole current flowing through an electrolyte solution. As the number of flowed electrons is the same as the number of moved ions, the transference number can be determined by calculating the quantity of electricity, namely, the number of electrons.

A theoretical calculation formula for the transference number is expressed by:

$$M \text{ (calculated value)} = (I \cdot t)/(F)$$

M: Molar number of flowed ions
F (Faraday constant): 96500 C/
I: Quantity of electricity (A: ampere)
t: Energized time (seconds)

3) According to the experimental results under the operation conditions (current: 0.3 mA) set from the standpoint of biosafety (safety to the skin), transference numbers by the iontophoresis devices previously proposed by the present inventors [see JP-A-2000-229128, JP-A-2000-237326 and JP-A-2000-237328; And these previously proposed iontophoresis devices lacked the idea that the elements (members) be all formed into thin membrane bodies] were as low as about 50% even after a long time (45 minutes later), although the constant current was set at 1 mA. The above-described transference number of 80% according to the present invention is, therefore, far superior.

4) The pH of the skin-simulating bath (A) was acidic (pH about 6.) at the energized time of 0 minute, and remained substantially unchanged even 35 minutes later. This is an advantageous effect which is attributed to the use of the ion exchange membranes on both electrode sections (1,2).

TABLE 1

Amount of ascorbic acid in the skin-simulating bath (A)

| Energized time | 0 min | 15 min | 20 min | 35 min |
|---|---|---|---|---|
| Amount of ascorbic acid in the skin-simulating bath after energization (micron mol) | 0.015 | 2.13 | 3.5 | 5.28 |

<Experiments on the Skin>

Using an iontophoresis device (X) of the construction shown in FIG. 4, iontophoresis experiments (transdermal delivery experiments) were actually conducted on the skin of animals and the skin of human volunteers. As base membranes for ionic-drug-retaining membranes and electrolyte-solution-retaining membranes, the above-described acrylic hydrogel membranes (microporous gel membranes) (products of the Sun Contact Lens Co., Ltd.) were used.

(1) Experimenting Equipment

An iontophoresis electrode section (1) connected to a galvanostat (constant-current generator) was constructed by bringing into close contact an anion exchange membrane (15), an ionic-drug-retaining membrane (14) impregnated with sodium ascorbate (100 mM), a cation exchange membrane (13), an electrolyte-solution-retaining membrane (12) impregnated with an electrolyte solution composed of an equiratio solution of 1 M lactic acid and 1 M sodium fumarate, and an electrode plate (11) in this order as viewed from the side of a skin-contacting surface. On the other hand, a ground electrode section (2) was constructed by bringing into close contact a cation exchange membrane (23), an electrolyte-solution-retaining membrane (24) impregnated with the above-described electrolyte solution, an anion exchange membrane (25), an electrolyte-solution-retaining membrane (22) impregnated with the above-described electrolyte solution, and an electrode plate (21) in this order as viewed from the side of a skin-contacting surface.

As the electrode plate (21) of the ground electrode section (2), a patch-type Red Dot monitoring electrode, commercial product, was used. Incidentally, this electrode also served to exhibit the function of the electrolyte-solution-retaining membrane (22). Further, a conductive gel (Aquasonic 100, product of Parker Laboratories, Inc.) was coated on a surface of the ion exchange membrane (23), at said surface the ground electrode section (2) to be brought into contact with the skin surface, to improve the conductivity.

(2) Experimenting Procedure

A color developer reagent, which intensifies the development of a color with time under the reducing action effect of ascorbic acid and causes precipitation of formazan (red color), was intradermally injected beforehand. Depending upon the extent of color development, the iontophoresis effect on ascorbic acid was determined.

Employed as the color developer reagent was a solution prepared by dissolving 2,3,5-triphenyltetrazorium chloride ($C_{19}H_{15}ClN_4$; hereinafter abbreviated as TTC) at a concentration of 2% in a 0.9% aqueous solution of NaCl. This color developer reagent has a property that, when subjected to reducing action, it couples with two molecules of hydrogen and forms a formazan compound (vivid crimson) to change its color.

The current applied in this experiment was set at 0.3 mA (constant current).

As a comparative experiment, on the other hand, ion non-exchange PP membranes were used instead of the ion exchange membranes. The PP membranes were polypropylene-made, microporous partitions (AN Filter, AN06, product of Nihon Millipore K.K.), and had no ion selective permeability.

(3) Experimental Results

The results are presented below in Table 2.

The ranking in Table 2 was made in accordance with the following system:

−: not reacted, ±: slightly reacted, +: apparently reacted, ++: pronouncedly reacted.

TABLE 2

| Energized time | | Chromogenic reaction |
|---|---|---|
| Ascorbic acid adsministered (ion exchange membranes used) | 15 min | + |
| | 20 min | ++ |
| | 35 min | ++ |

TABLE 2-continued

| Energized time | | Chromogenic reaction |
|---|---|---|
| Control | 15 min | – |
| Ascorbic acid administered | 20 min | ± |
| (PP membranes used) | 35 min | + |

From those experiments, the following findings were obtained.

1) When the ion exchange membranes were used in accordance with the above-described embodiment of the present invention, the color development reached the maximum in 20 minutes. When the ion nonexchange PP membranes were used in place of the ion exchange membranes, the reaction was observed as late as 35 minutes, and it was 60 minutes later that the color development reached the maximum value. The effectiveness of use of ion exchange membranes in accordance with the embodiment of the present invention was, therefore, proven on the skin of the body.

2) In the experiments, no skin alteration was observed at all on the side of the ground electrodes.

3) Variations in the applied voltage (initial voltages: 10 V) were within as small as about 1 V, although a current was applied at 0.3 mA, which falls within a current range safe for the body, for 35 minutes or longer. This has proven that a 1:1 aqueous solution of 1 M lactic acid and 1 M sodium fumarate is useful as an electrolyte solution, and also suggests that, as lactic acid and fumaric acid are both organic acids existing in the body, use of physiological organic acids other than lactic acid and fumaric acid is safe.

<Embodiment of Iontophoresis Device (Hardware Construction)>

Next, with reference to the drawings, a description will be made in detail about an embodiment of the iontophoresis device (X) according to the present invention, which is useful for administering an ionic drug by iontophoresis, especially from the viewpoint of the elements of the device (equipment) (hardware construction).

In the drawings, some elements (members), connection modes of elements (members) themselves, or some hatching may be omitted in some instances to clarify the illustration. Further, the thickness of each thin membrane body does not represent the accurate thickness to improve the clarity of the illustration.

Nonetheless, the features omitted in the drawings can be readily understood from the description of the individual embodiments and the accompanying drawings.

FIG. 1 to FIG. 2 illustrate the first embodiment of the iontophoresis device (X) according to the present invention, in which FIG. 1 is the perspective view of the entire device and FIG. 2 is a partly cut-off cross-sectional view.

As shown in FIG. 1 to FIG. 2, the iontophoresis device (X) according to the first embodiment of the present invention comprises the following three elements:

(i) the cylindrical iontophoresis electrode section (1), (ii) the cylindrical ground electrode section (2) constructed as a discrete (non-integral) unit relative to the cylindrical iontophoresis electrode section (1), and (iii) This constant current and constant voltage power source (3) may hereinafter be called simply the power source (3).

In the iontophoresis device (X) according to the first embodiment of the present invention, the ground electrode section (2) is constructed as a discrete unit relative to the iontophoresis electrode section (1). The expression constructed as a discrete unit as used above means that as illustrated in the drawings, the iontophoresis electrode section (1) and the ground electrode section (2) are not integral. The iontophoresis device (X) has, for example, such a structure that an iontophoretically treated patient holds the ground electrode section (2) or brings the ground electrode section (2) into contact with a desired skin surface, other than a treated site to establish grounding.

The iontophoresis device (X) according to the first embodiment of the present invention shown in FIG. 1 to FIG. 2 was constructed under the premise that sodium ascorbate ($As^-Na^+$) is administered as an ionic drug.

Accordingly, the reference numerals of the respective elements (the electrode plates, the electrolyte-solution-retaining membranes, the ionic-drug-retaining membrane, and the ion exchange membranes) arranged inside the iontophoresis device (X) shown in FIG. 1 to FIG. 2 indicate the same elements described above with reference to FIG. 3.

The iontophoresis electrode section (1) in the iontophoresis device (X) according to the first embodiment of the present invention is constructed of the following two elements as illustrated in FIG. 1 to FIG. 2:

(i) the non-conductive, small-diameter, cylindrical end section ($1a$), and (ii) the non-conductive, large-diameter, cylindrical grip section ($1b$).

The end section ($1a$) is constructed such that it can be detachably mounted on a front portion ($1b_1$) of the grip section ($1b$), and within the end section ($1a$), the elements designated by reference numerals (11 to 15) are held or accommodated.

The elements ($1a$,$1b$) can be made of nonconductive plastics, for example.

As illustrated in FIG. 2, the cylindrical end section ($1a$) is composed of a front portion ($1a_1$), a main portion ($1a_2$), and a lock portion ($1a_3$) kept in engagement with the grip section ($1b$). The front portion ($1a_1$) has an opening ($1a_{11}$) and is constructed such that the anion exchange membrane (15) is exposed in the opening.

As also shown in FIG. 2, the cylindrical grip section ($1b$), on the other hand, is composed of the front portion ($1b_1$), a main portion ($1b_2$), and a rear end portion ($1b_3$). The front portion ($1b_1$) has an opening ($1b_{11}$) of substantially the same diameter as the main portion ($1a_2$) of the end section ($1a$) and is constructed to define lock holes ($1b_{12}$) for guiding the lock portion ($1a_3$) such that the lock portion ($1a_3$) of the cylindrical end section ($1a$) is locked on the front portion ($1b_1$).

Further, the cylindrical grip section ($1b$) is constructed to have a spring holding wall ($1b_4$) for fixedly supporting a spring member (33) accommodated within the cylindrical grip section ($1b$) and made of a conductive material. The spring holding wall ($1b_4$) is constructed such that, as illustrated in FIG. 2, a free end of a cable (31) from the power source (3) and the spring member (33) are electrically connected.

Detachable mutual locking of both of the elements ($1a$,$1b$) can be achieved by the lock portion ($1a_3$) of the cylindrical end section ($1a$) and the lock holes ($1b_{12}$) of the cylindrical grip section ($1b$). Described specifically, the lock portion ($1a_3$) is inserted into the lock holes ($1b_{12}$), respectively, and the cylindrical end section ($1a$) is turned clockwise or counterclockwise to lock them together. Incidentally, they are stably and detachably locked together because spring force is exerted by the spring member (33) on the cylindrical end section ($1a$) (to urge the same).

The ground electrode section (2) in the iontophoresis device (X) according to the first embodiment of the present invention is constructed of the following two elements as illustrated in FIG. 1 to FIG. 2:

(i) a non-conductive, small-diameter, cylindrical end section (2a), and (ii) a non-conductive, large-diameter, cylindrical main section (2b).

Both of the elements (2a,2b) are constructed such that the end section (2a) can be detachably mounted on the main section (2b) by a similar mechanism as in the elements (1a, 1b) in the iontophoresis electrode section (1).

The elements (21,22,23) are accommodated inside the small-diameter, cylindrical end section (2a) as depicted in FIG. 2. Further, a conductive spring member (34) is accommodated inside the large-diameter, cylindrical main section (2b). An end portion of the spring member (34) is fixedly supported on a bottom part of the large-diameter, cylindrical main section (2b) and is also connected with an end portion of a cable (32) from the power source (3). Its opposite end portion, on the other hand, urges the element (21), namely, the electrode plate (21) in the ground electrode (2) under spring force, and also urges the cylindrical end section (2a) under spring force such that the locking between the cylindrical end section (2a) and the main section (2b) can be assured.

As a modification of the iontophoresis device according to the first embodiment of the present invention, the power source (3) may be replaced by a cell, and this cell may be accommodated within the internal space of the large-diameter, cylindrical grip section (1b).

Figure 6:
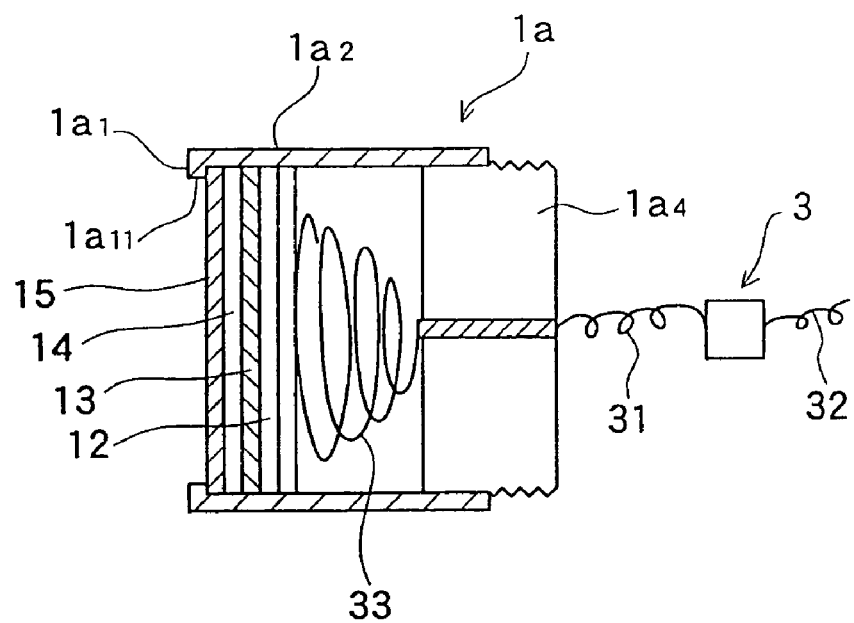
FIG. 6 is a view illustrating an iontophoresis device (X) according to a second embodiment of the present invention, and is a view corresponding to a small-diameter, cylindrical end section (1a) in FIG. 2.

FIG. 6 is the view illustrating the second embodiment of the iontophoresis device according to the present invention, and corresponds to the small-diameter, cylindrical end section (1a) in FIG. 2 which pertains to the first embodiment.

The second embodiment adopts a different construction of the small-diameter cylindrical end section (1a) from that of the first embodiment (see FIG. 2), in which a small-diameter cylindrical end section (1a) is constructed to arrange a bottom cover (1a₄), which is equipped with a thread groove or slide guide grooves, on a rear end part of a main portion (1a₂) of the front end section (1a). The main portion (1a₂) is provided on an inner wall of the rear end part thereof with groove(s) corresponding to the thread groove or slide guide grooves in the bottom cover (1a₄), and by these grooves, the bottom cover (1a₄) is fixed to the main portion (1a₂). In this embodiment, the urging force applied by the spring member (33) can be adjusted.

Figure 7:
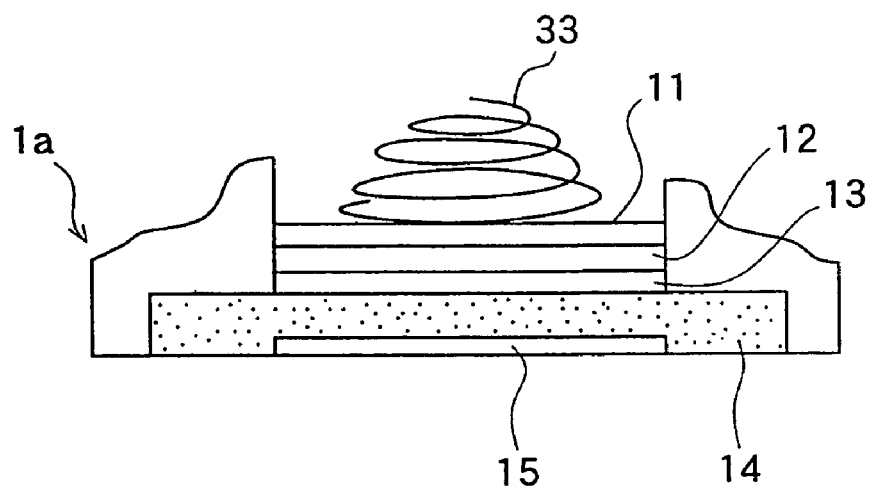
FIG. 7 is a view illustrating an iontophoresis device (X) according to a third embodiment of the present invention, and is a view corresponding to an end portion of the small-diameter, cylindrical end section (1a) in FIG. 2.

FIG. 7 is the view illustrating the third embodiment of the iontophoresis device according to the present invention, and corresponds to the front part of the small-diameter, cylindrical end section (1a) in FIG. 2 which pertains to the first embodiment.

A characteristic feature of the third embodiment is that an ionic-drug-retaining membrane (14) is extended outward so as to form a concentric circular part as well beyond the outer circumference of a circular anion exchange membrane (15).

In this case, use of a gel membrane having good adhesion to the skin, for example, GELLODE (trade name, product of Takiron Co., Ltd.), specifically the segmented polyurethane gel membrane having PEG-PPG segments or the like as a membrane (microporous gel membrane), which serves as a base of the ionic-drug-retaining membrane (14), has a merit in that adhesion of the anion exchange membrane (15) to the skin surface can be assured.

Although the third embodiment is a modification of the above-described first embodiment, it can be used as a modification of the second embodiment.

Figure 8:
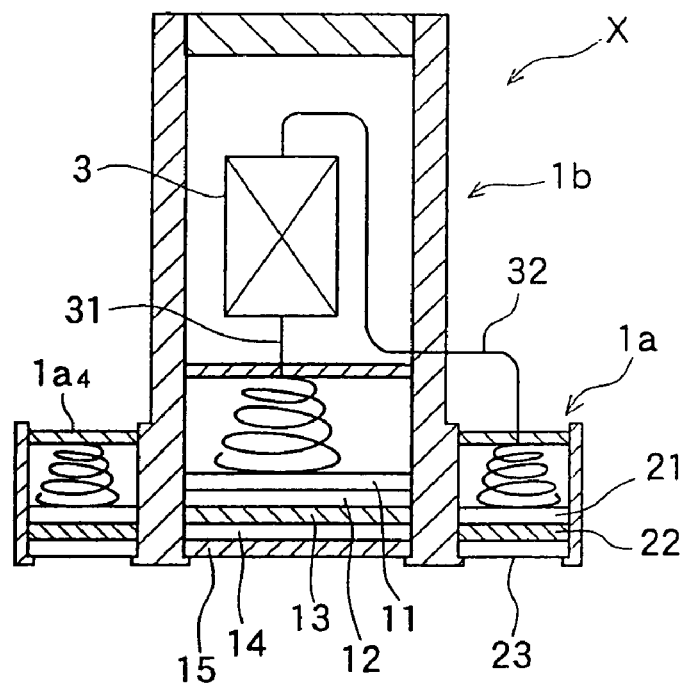
FIG. 8 is a view (cross-sectional view) for illustrating an iontophoresis device (X) according to a fourth embodiment of the present invention.
Figure 9:
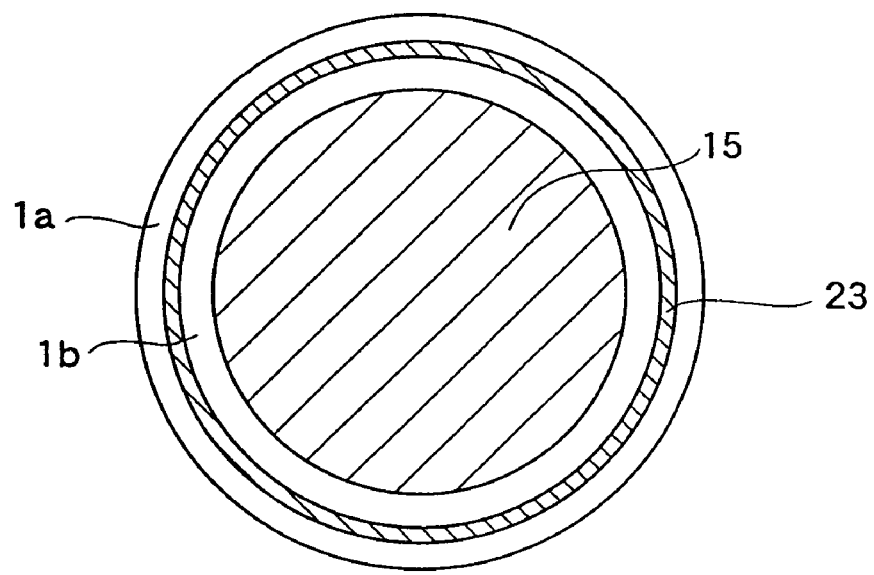
FIG. 9 is a front view of the iontophoresis device (X) according to the fourth embodiment of FIG. 8.

FIG. 8 to FIG. 9 illustrate the iontophoresis device (X) according to the fourth embodiment of the present invention, in which FIG. 8 is its cross-sectional view and FIG. 9 is its front view.

In an elongated iontophoresis electrode section (1) in this fourth embodiment, an elongated, cylindrical main section (1b) serves as a grip section, and the above-described elements (11 to 15), spring member (33) and power source (3) are accommodated inside the main section (1b).

A ground electrode section (2), on the other hand, is constructed in substantially the same structure as the cylindrical end section (1a) in the second embodiment (see FIG. 6). The elements (21 to 23) accommodated inside the cylindrical end section (1a) of the ground electrode section (2) are different from the elements (11 to 15) in the second embodiment because this part becomes the ground electrode section (2) in the fourth embodiment.

In the fourth embodiment, the operator (user) of the iontophoresis device (X) is no longer required to establish grounding by holding the ground electrode section (2), unlike the first to third embodiments, and therefore, the fourth embodiment brings about improved convenience.

Further, the ground electrode section (2) can effectively establish grounding because it is arranged at a position close to the iontophoresis electrode section (1).

I. Advantageous Effects

According to the present invention, excellent advantageous effects can be brought about as will be described next:

(i) In the iontophoresis electrode section (active electrode section) and the ground electrode section (inactive electrode section), especially the ionic drug and electrolytic solutions are retained in specific, impregnatedly-retaining membranes, and ion exchange membranes having different ion selectivity are arranged in a specific order. Under the above-described specific construction, a stably energized state (constant current and/or constant voltage) can be maintained for a long period of time. In the iontophoresis electrode section, the active ingredient of the ionic drug, said active ingredient being charged positive (+) or negative (−), can be delivered (drug delivery) efficiently at a high transference number to the skin (or the mucosa).

(ii) The iontophoresis electrode section (active electrode section) and the ground electrode section contribute to the maintenance of the above-described stable energized state for a long period of time, and the use (arrangement) of particular ion exchange membranes on the both electrode sections can eliminate the deleterious effects on the skin through electrode reactions.

(iii) In the iontophoresis electrode section (active electrode section) and the ground electrode section, the elements relevant to the delivery of ions are all formed into thin membrane bodies, including the electrode plates. The device is, therefore, provided with significant improvements in convenience such as compactness, maintainability, and handling ease (including ease in replacing members).

(iv) In the iontophoresis device according to the present invention, some of the individual elements (members) which make up the electrode sections (active electrode section and ground electrode section), specifically the electrode plates, electrolyte-solution-retaining membranes, ionic-drug-retaining membrane and ion (cation and anion) exchange membranes can be assembled into kits beforehand. Depending on the various therapeutic purposes, membrane bodies retaining desired drug solutions or drug solutions of desired concentrations in such a state that the membrane bodies are impregnated with the desired drug solutions or the drug solutions of the desired concentrations, can be prepared into kits beforehand. Upon using the iontophoresis device, an operator (user) can select desired ones of the kits, depending upon the therapeutic purpose and can assemble them easily. This leads to significant improvements in the convenience of the device.

In addition, the subassembly into such kits makes it possible to achieve a reduction in the size of the device, prevention of treatment errors (because the elements have been sub-assembled into kits), or the like.

INDUSTRIAL APPLICABILITY

The iontophoresis device according to the present invention can transdermally deliver an ionic drug at high efficiency under stable energized conditions for a long period of time.

The iontophoresis device according to the present invention is also excellent in safety, because ion exchange membranes are arranged on the side of the active electrode section and also on the side of the ground electrode section not only from the viewpoint of transference number of the ionic drug but also from the viewpoint of assuring high safety to the skin.

In the iontophoresis device according to the present invention, both of the electrode sections are constructed of thin membrane bodies in their entirety. Subassembly or the like of these thin membrane bodies into kits is effective for forming the device into a smaller size and also for making the device excellent in ease in replacing its members (parts), in preventing treatment errors and also in handling.

Although iontophoresis treatments of this type have been proposed the iontophoresis device according to the present invention equipped with various meritorious characteristics as mentioned above, is a really practical device, and its industrial value is significant.

The invention claimed is:

1. An iontophoresis device useful for administering an ionic drug by iontophoresis, said iontophoresis device having an iontophoresis electrode section (active electrode section) and a ground electrode section (inactive electrode section) both of which are connected to a power source, comprising
    (1) said iontophoresis electrode section comprises:
    (1)-1. an electrode plate connected to said power source of the same polarity as the charged ions of said ionic drug,
    (1)-2. an electrolyte-solution-retaining membrane arranged on a front side of said electrode plate and retaining therein an electrolyte solution in such a state that said electrolyte-solution-retaining membrane is impregnated with said electrolyte solution,
    (1)-3. an ion exchange membrane arranged on a front side of said electrolyte-solution-retaining membrane and selective to ions opposite in polarity to said charged ions of said ionic drug,
    (1)-4. an ionic-drug-retaining membrane arranged on a front side of said ion exchange membrane and retaining therein said ionic drug in such a state that said ionic-drug-retaining membrane is impregnated with said ionic drug, and
    (1)-5. an ion-exchange membrane arranged on a front side of said ionic-drug-retaining membrane and selective to ions of the same species as said charged ions of said ionic drug; and
    (2) said ground electrode section comprises:
    (2)-1. an electrode plate opposite in polarity to said electrode plate in said iontophoresis electrode section,
    (2)-2. an electrolyte-solution-retaining membrane arranged on a front side of said electrode plate and retaining therein an electrolyte solution in such a state that said electrolyte-solution-retaining membrane is impregnated with said electrolyte solution, and
    (2)-3. an ion exchange membrane arranged on a front side of said electrolyte-solution-retaining membrane and selective to ions opposite in polarity to said charged ions of said ionic drug,
    wherein two said electrolyte-solution-retaining membranes in both said introphoresis and ground electrode sections retain therein an electrolyte solution containing one or more compounds which have an oxidation-reduction potential lower than the oxidation-reduction potential of water in electrolysis in such a state that two said electrolyte-solution-retaining membranes are impregnated with said electrolyte solution, and said electrolyte solution contains (1) lactic acid and sodium fumarate, or (2) ferrous sulfate and ferric sulfate.

2. The iontophoresis device according to claim 1, wherein:
    (2) said ground electrode section comprises:
    (2)-1. an electrode plate opposite in polarity to said electrode plate in said iontophoresis electrode section,
    (2)-2. an electrolyte-solution-retaining membrane arranged on a front side of said electrode plate and retaining therein an electrolyte solution in such a state that said electrolyte-solution-retaining membrane is impregnated with said electrolyte solution,
    (2)-5. an ion exchange membrane arranged on a front side of said electrolyte-solution-retaining membrane and selective to ions of the same species as said charged ions of said ionic drug,
    (2)-4. an electrolyte-solution-retaining membrane arranged on a front side of said ion exchange membrane and retaining therein an electrolyte solution in such a state that said electrolyte-solution-retaining membrane is impregnated with said electrolyte solution, and
    (2)-3. an ion exchange membrane arranged on a front side of said electrolyte-solution-retaining membrane and selective to ions opposite in polarity to said charged ions of said ionic drug,
    wherein three said electrolyte-solution-retaining membranes in both said introphoresis and ground electrode sections retain therein an electrolyte solution containing one or more compounds which have an oxidation-reduction potential lower than the oxidation-reduction potential of water in electrolysis in such a state that three said electrolyte-solution-retaining membranes are impregnated with said electrolyte solution, and said electrolyte solution contains (1) lactic acid and sodium fumarate, or (2) ferrous sulfate and ferric sulfate.

3. The iontophoresis device according to claim 1, wherein said iontophoresis electrode section is constructed of assembling elements, comprising of said electrode plate, said electrolyte-solution-retaining membrane, said ionic-drug-retaining membrane, and said two ion exchange membranes, some or all of which have been assembled into one or more kits beforehand.

4. The iontophoresis device according to claim 3, wherein said electrode plate and said electrolyte-solution-retaining membrane of said assembling elements have been assembled into a kit beforehand.

5. The iontophoresis device according to claim 3, wherein said ionic-drug-retaining membrane and two said ion exchange membranes of said assembling elements have been assembled into a kit beforehand.

6. The iontophoresis device according to claim 1, wherein said ground electrode section is constructed of assembling elements, comprising of said electrode plate, said electrolytesolution-retaining membrane and said ion exchange membrane, some or all of which have been assembled into one or more kits beforehand.

7. The iontophoresis device according to claim 6, wherein said electrode plate and said electrolyte-solution-retaining membrane of said assembling elements have been assembled into a kit beforehand.

8. The iontophoresis device according to claim 6, wherein said electrode plate, said electrolyte-solution-retaining membrane and said ion exchange membrane of said assembling elements have been assembled into a kit beforehand.

9. The iontophoresis device according to claim 1, wherein two said electrolyte-solution-retaining membranes in both said introphoresis and ground electrode sections and said ionic-drug-retaining membrane in said iontophoresis electrode section comprise of an acrylic hydrogel membrane having a degree of impregnation of 30 to 40%.

10. The iontophoresis device according to claim 1, wherein said iontophoresis electrode section and said ground electrode section are constructed into discrete units.

11. The iontophoresis device according to claim 1, wherein said iontophoresis electrode section and said ground electrode section are constructed into an integral structure.

12. The iontophoresis device according to claim 2, wherein said iontophoresis electrode section is constructed of assembling elements, comprising of said electrode plate, said electrolyte-solution-retaining membrane, said ionic-drug-retaining membrane, and two said ion exchange membranes, some or all of which have been assembled into one or more kits beforehand.

13. The iontophoresis device according to claim 12, wherein said electrode plate and said electrolyte-solution-retaining membrane of said assembling elements have been assembled into a kit beforehand.

14. The iontophoresis device according to claim 12, wherein said ionic-drug-retaining membrane and two said ion exchange membranes of said assembling elements have been assembled into a kit beforehand.

15. The iontophoresis device according to claim 2, wherein said ground electrode section is constructed of assembling elements, comprising of said electrode plate, two said electrolyte-solution-retaining membranes, and two said ion exchange membranes, some or all of which have been assembled into one or more kits beforehand.

16. The iontophoresis device according to claim 15, wherein said electrode plate and said electrolyte-solution-retaining membrane, arranged on a front side of said electrode plate, of said assembling elements have been assembled into a kit beforehand.

17. The iontophoresis device according to claim 15, wherein two said ion exchange membranes and said electrolyte-solution-retaining membrane disposed between two said ion exchange membranes of said assembling elements have been assembled into a kit beforehand.

18. The iontophoresis device according to claim 2, wherein three said electrolyte-solution-retaining membranes in both said introphoresis and ground electrode sections and said ionic-drug-retaining membrane in said iontophoresis electrode section comprise of an acrylic hydrogel membrane having a degree of impregnation of 30 to 40%.

19. The iontophoresis device according to claim 2, wherein said iontophoresis electrode section and said ground electrode section are constructed into discrete units.

20. The iontophoresis device according to claim 2, wherein said iontophoresis electrode section and said ground electrode section are constructed into an integral structure.

* * * * *